US009592275B2

(12) United States Patent
Tsuruta et al.

(10) Patent No.: US 9,592,275 B2
(45) Date of Patent: *Mar. 14, 2017

(54) MEDICAMENT FOR THERAPEUTIC TREATMENT AND/OR IMPROVEMENT OF SEPSIS

(71) Applicant: ASAHI KASEI PHARMA CORPORATION, Tokyo (JP)

(72) Inventors: Kazuhisa Tsuruta, Tokyo (JP); Yoshikazu Aoki, Tokyo (JP); Yutaka Osawa, Tokyo (JP); Inder Kaul, Waltham, MA (US)

(73) Assignee: ASAHI KASEI PHARMA CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/358,115

(22) PCT Filed: Nov. 14, 2012

(86) PCT No.: PCT/JP2012/079449
§ 371 (c)(1),
(2) Date: Feb. 23, 2015

(87) PCT Pub. No.: WO2013/073545
PCT Pub. Date: May 23, 2013

(65) Prior Publication Data
US 2015/0157695 A1 Jun. 11, 2015

Related U.S. Application Data

(60) Provisional application No. 61/559,864, filed on Nov. 15, 2011.

(51) Int. Cl.
| A61K 38/36 | (2006.01) |
| A61K 38/57 | (2006.01) |
| A61K 38/00 | (2006.01) |
| C12N 15/09 | (2006.01) |
| A61K 38/17 | (2006.01) |

(52) U.S. Cl.
CPC ............ *A61K 38/366* (2013.01); *A61K 38/00* (2013.01); *A61K 38/177* (2013.01); *A61K 38/57* (2013.01); *C12N 15/09* (2013.01)

(58) Field of Classification Search
None
See application file for complete search history.

(56) References Cited

U.S. PATENT DOCUMENTS

| 5,043,425 A | 8/1991 | Aoki et al. |
| 5,202,421 A | 4/1993 | Kunihiro et al. |
| 5,300,490 A | 4/1994 | Kunihiro et al. |
| 5,466,668 A | 11/1995 | Glaser et al. |
| 5,516,659 A | 5/1996 | Nii et al. |
| 5,574,007 A | 11/1996 | Zushi et al. |
| 5,695,964 A | 12/1997 | Nii et al. |
| 5,753,123 A | 5/1998 | Kajihara et al. |
| 5,827,824 A | 10/1998 | Light et al. |
| 6,034,060 A | 3/2000 | Yamamoto et al. |
| 6,063,763 A | 5/2000 | Light et al. |
| 8,258,269 B2 | 9/2012 | Ohigashi |
| 8,293,710 B2 | 10/2012 | Wu et al. |
| 8,772,239 B2 | 7/2014 | Tsuruta et al. |
| 8,952,137 B2 | 2/2015 | Ohigashi |
| 9,034,823 B2 | 5/2015 | Tsuruta et al. |
| 2003/0139339 A1 | 7/2003 | Creasey |
| 2006/0083733 A1 | 4/2006 | Nishio |
| 2006/0148706 A1 | 7/2006 | Wu et al. |
| 2010/0145020 A1 | 6/2010 | Ohigashi |
| 2013/0237693 A1 | 9/2013 | Ohigashi |

FOREIGN PATENT DOCUMENTS

| CN | 1151406 A | 6/1997 |
| CN | 101024072 A | 8/2007 |
| CN | 101641368 A | 2/2010 |
| EP | 0312598 A1 | 4/1989 |
| EP | 0356836 A2 | 3/1990 |
| EP | 0376251 A2 | 7/1990 |
| EP | 2-255699 A | 10/1990 |
| EP | 0412841 A1 | 2/1991 |
| EP | 3-133380 A | 6/1991 |
| EP | 3-218399 A | 9/1991 |
| EP | 0445681 A2 | 9/1991 |
| EP | 0474273 A2 | 3/1992 |
| EP | 0489180 A1 | 6/1992 |
| EP | WO 2008/038777 A1 | 4/2008 |
| JP | 64-6219 A | 1/1989 |
| JP | 3-86900 A | 4/1991 |
| JP | 3-259084 A | 11/1991 |

(Continued)

OTHER PUBLICATIONS

Office Action issued May 5, 2015, in Canadian Patent Application No. 2,854,882.
Office Action issued May 12, 2015, in Japanese Patent Application No. 2013-544281, with English translation.
Report No. 1 issued May 12, 2015, in Australian Patent Application No. 2012337838.
First Examination Report issued Feb. 20, 2015, in New Zealand Patent Application No. 624542.
First Office Action issued Feb. 17, 2017, in Chinese Patent Application No. 201280055832.2, with English translation.
Mohri et al., "The antithrombotic effects of recombinant human soluble thrombomodulin (rhsTM) on tissue factor-induced disseminated intravascular coagulation in crab-eating monkeys (*Macaca fascicularis*)," Blood Coagulation and Fibrinolysis (1997), vol. 8, pp. 274-283.

(Continued)

*Primary Examiner* — James H Alstrum Acevedo
*Assistant Examiner* — Tara Martinez
(74) *Attorney, Agent, or Firm* — Birch, Stewart, Kolasch & Birch, LLP

(57) ABSTRACT

A medicament for therapeutic treatment and/or improvement of sepsis in a patient with severe sepsis accompanied with one or more organ dysfunctions, wherein a value of International Normalized Ratio (INR) of a plasma specimen obtained from said patient is more than 1.4, which comprises thrombomodulin as an active ingredient.

1 Claim, No Drawings

(56) References Cited

FOREIGN PATENT DOCUMENTS

| | | |
|---|---|---|
| JP | WO 92/00325 A1 | 1/1992 |
| JP | 4-210700 A | 7/1992 |
| JP | 5-213998 A | 8/1993 |
| JP | 2005-515214 A | 5/2005 |
| WO | WO 92/03149 A1 | 3/1992 |
| WO | WO 93/15755 A1 | 8/1993 |
| WO | WO 03/055442 A2 | 7/2003 |
| WO | WO 03/061687 A1 | 7/2003 |
| WO | WO 2008/073884 A2 | 6/2008 |
| WO | WO 2009/007112 A2 | 1/2009 |
| WO | WO 2010/006634 A1 | 1/2010 |

OTHER PUBLICATIONS

Takahashi et al., "Human Urinary Soluble Thrombomodulin (MR-33) Improves Disseminated Intravascular Coagulation without Affecting Bleeding Time in Rats: Comparison with Low Molecular Weight Heparing," Thrombosis and Haemostasis (1997), vol. 77, No. 4, pp. 789-795.

32nd ISICEM—International Symposium on Intensive Care and Emergency Medicine, Brussels, Belgium Congress Center, Mar. 20-23, 2012, 39 pages.

Abraham et al., "Assessment of the safety of recombinant tissue factor pathway inhibitor in patients with severe sepsis: A multi-center, randomized, placebo-controlled, single-blind, dose escalation study", Critical Care Medicine, vol. 29, No. 11, 2001, pp. 2081-2089.

Abraham et al., "Efficacy and Safety of Tifacogin (Recombinant Tissue Factor Pathway Inhibitor) in Severe Sepsis", JAMA, vol. 290, No. 2 (Reprinted), Jul. 9, 2003, pp. 238-247.

Aikawa et al., "Thrombomodulin Alfa in the Treatment of Infectious Patients Complicated by Disseminated Intravascular Coagulation: Subanalysis From the Phase 3 Trial", Shock, vol. 35, No. 4, 2011, pp. 349-354.

Asahi Kasei Pharma America Corporation, "Summary of ART-123 Global Phase 2b Study", 2012, 16 pages.

Asahi Kasei Pharma Corporation, "Recomodulin® Inj. 12800", Use-results Survey (All-Case Surveillance), Report on Results of Last Collection (Summary), Infections, From the 5th periodic safety report, Jun. 2011, cover page and pp. 1-23 (59 pages total), with English translation.

Bates et al., "New anticoagulants: beyond heparin, low-molecular-weight heparin and warfarin", British Journal of Pharmacology, vol. 144, No. 8, 2005 (published online Feb. 15, 2005), pp. 1017-1028.

Bernard et al., "Efficacy and Safety of Recombinant Human Activated Protein C for Severe Sepsis", The New England Journal of Medicine, vol. 344, No. 10, Mar. 8, 2001, pp. 699-709.

Bone et al., "The ACCP-SCCM Consensus Conference on Sepsis and Organ Failure", CHEST Editorials, vol. 101, No. 6, Jun. 1992, Downloaded From: http://journal.publications.chestnet.org on Dec. 18, 2012, pp. 1481-1483.

Endo et al., "Clinical experience of recombinant thrombomodulin . . . ", D0-55-4, General Session: Oral 55 Multiple Oral Failure, Day 3, 10:00-11:00, Venue 6 (1002), Journal of the Japanese Society of Intensive Care Medicine, vol. 16 (Suppl), 2009, p. 266 (3 pages total), with English translation.

Endo et al., "Has Survival Rate of Sepsis Improved by Surviving Sepsis Campaign Guideline (SSCG) 2008?", Shock, vol. 26, No. 2, 2011, pp. 58-66 (21 pages total), with English translation.

Fareed et al., "2223 Dysregulation of Inflammatory and Hemostatic Markers in Sepsis Associated Disseminated Intravascular Coagulation", 54th ASH Annual Meeting and Exposition, Atlanta, GA, American Society of Hematology, Dec. 8-11, 2012, 1 page.

Gomi et al., "Antithrombotic Effect of Recombinant Human Thrombomodulin on Thrombin-Induced Thromboembolism in Mice", Blood, vol. 75, No. 7, Apr. 1, 1990, pp. 1396-1399.

Hoppensteadt et al., "1131 Thrombin Generation Mediators and Markers in Sepsis Associated Coagulopathy and Their Modulation by Recombinant Thrombomodulin", 54th ASH Annual Meeting and Exposition, Atlanta, GA, Dec. 8-11, 2012, American Society of Hematology, 1 page.

Ikeda, "Diagnosis and Treatment of Severe Sepsis and Septic Shock", Surgery Frontier, vol. 19, No. 2, 2012, pp. 125-131 (16 pages total), with English translation.

Inao et al., "Therapeutic efficacy of recombinant thrombomodulin in acute lung injury in the mouse . . . ", O-1-311, 37th Annual Meeting of the Japanese Assn. for Acute Medicine, Journal of Japanese Assn. for Acute Medicine, vol. 20, No. 8, Aug. 15, 2009, p. 512 (4 pages total), with English translation.

International Preliminary Report on Patentability and Written Opinion of the International Searching Authority (Forms PCT/IB/326, PCT/IB/338, PCT/IB/373 and PCT/ISA/237) issued May 30, 2014, in PCT International Application No. PCT/JP2012/079449, with English translation.

International Search Report and Written Opinion of the International Searching Authority (Forms PCT/ISA/210, PCT/ISA/220 and PCT/ISA/237), dated Feb. 19, 2013, for International Application No. PCT/JP2012/079449, with English Excerpts.

Ishikura, "IV Treatment of Sepsis in ICU", Q26 Anticoagulation therapy, Emergency & Critical Care, vol. 24, No. 9/10, 2012, pp. 1168-1176 (21 pages total), with English translation.

Isotani et al., "Therapeutic efficacy of Recomodulin in multiple organ failure associated with sepsis", Session Number: G-21 (D), Journal of Japanese Society for Emergency Medicine, vol. 13, No. 2, 2010, p. 206 (3 pages total), with English translation.

Isotani et al., "Therapeutic strategy in multiple organ failure associated with sepsis", PD10-4, Journal of Japanese College of Surgeons, vol. 35, No. 3, 2010, p. 422 (4 pages total), with English translation.

Kaul et al., "24 A Randomized, Double-Blind, Placebo-Controlled, Phase-2B Study to Evaluate the Safety and Efficacy of Recombinant Human Soluble Thrombomodulin, ART-123, in Patients with Sepsis . . . ", 54th ASH Annual Meeting and Exposition, Atlanta, GA, Dec. 8-11, 2012, Abstract only (1 page).

Kaul et al., "A Randomized, Double-Blind, Placebo-Controlled, Phase-2B Study to Evaluate the Safety and Efficacy of Recombinant Human Soluble Thrombomodulin, ART-123 . . . ", Presentation Materials for 54th ASH Annual Meeting and Exposition, Atlanta, GA, Dec. 8-11, 2012, 12 pages.

Levy et al., "2001 SCCM/ESICM/ACCP/ATS/SIS International Sepsis Definitions Conference", Critical Care Medicine, vol. 31, No. 4, 2003, pp. 1250-1256.

Levy et al., "The Surviving Sepsis Campaign: results of an international guideline-based performance improvement program targeting severe sepsis", Intensive Care Medicine, vol. 36, 2010 (published online Jan. 13, 2010), pp. 222-231.

Nakahara et al., "Clinical efficacy of recombinant thrombomodulin in patients with disseminated intravascula coagulation associated with acute biliary infection", Japanese Journal of Medicine and Pharmaceutical Science, vol. 66, No. 1, Jul. 2011, pp. 111-115 (11 pages total), with English translation.

Nakahara et al., "Efficacy of recombinant soluble thrombomodulin in disseminated intravascular coagulation associated with sepsis", 12AP4-8, European Journal of Anaesthesiology, vol. 28, Suppl. 48, Jun. 2011, p. 177 and Abstract No. 12AP4-8 (2 pages total).

Okabayashi et al., "Hemostatic Markers and the Sepsis-Related Organ Failure Assessment Score in Patients With Disseminated Intravascular Coagulation in an Intensive Care Unit", American Journal of Hematology, vol. 76, 2004, pp. 225-229.

Saito et al., "Efficacy and safety of recombinant human soluble thrombomodulin (ART-123) in disseminated intravascular coagulation: results of a phase III, randomized, double-blind clinical trial", Journal of Thrombosis and Haemostasis, vol. 5, 2007, pp. 31-41.

Sakamoto et al., "Experience of Treatment in Septic Shock Cases PMMA-CHDF and Anticoagulation therapy (AT-III and rTM)", III Actual Treatment of Shock in Clinical Cases, Kyukyulgaku, vol. 35, 2011, pp. 466-469 (10 pages total), with English translation.

Suzuki, "Protein C Deficiency Disorder", Progress of Medicine, vol. 125, No. 11, Jun. 11, 1983, pp. 901-910 (11 pages total), with partial English translation.

(56) References Cited

OTHER PUBLICATIONS

Takagi et al., "Successful Administration of Recombinant Human Soluble Thrombomodulin α (Recomodulin) for Disseminated Intravascular Coagulation during Induction Chemotherapy in an Elderly Patient . . . ", Case Reports in Hematology, vol. 2011, Article ID 273070, 2011, 5 pages.
The Japanese Society of Intensive Care Medicine, "The Japanese Guidelines for the Management of Sepsis", 2012, pp. 0-12 (30 pages total), with English translation.
The STOP Sepsis Bundle Toolkit, Strategies to Timely Obviate the Progression of Sepsis, for the STOP Sepsis Working Group, Version 9.3, Sep. 2006, 24 pages.
U.S. Corrected Notice of Alllowability dated May 30, 2014 for U.S. Appl. No. 13/676,248.
U.S. Examiner Interview Summary dated Jan. 6, 2014, for U.S. Appl. No. 13/676,248.
U.S. Notice of Allowance dated Feb. 28, 2014 for U.S. Appl. No. 13/676,248.
U.S. Office Action dated Aug. 1, 2013 for U.S. Appl. No. 13/897,100.
U.S. Office Action dated dated Jul. 31, 2013 for U.S. Appl. No. 13/676,248.
Wen et al., "Human Thrombomodulin: Complete cDNA Sequence and Chromosome Localization of the Gene", Biochemistry, vol. 26, No. 14, 1987, pp. 4350-4357.
Yamakawa et al., "Evidence as for effectiveness of a medicament for treatment of DIC in medical care of sepsis—Effect of human recombinant-type thrombomodulin preparation", Journal of Japanese Association for Acute Medicine, vol. 22, 2011, p. 369 (3 pages total), with English translation.
Yamakawa et al., "Treatment effects of recombinant human soluble thrombomodulin in patients with severe sepsis: a historical control study", Critical Care, 15:R123, 2011, pp. 1-10.
Zushi et al., "The Last Three Consecutive Epidermal Growth Factor-like Structures of Human Thrombomodulin Comprise the Minimum Functional Domain for Protein C-activating Cofactor Activity . . . ", The Journal of Biological Chemistry, vol. 264, No. 18, Issue of Jun. 25, 1989, pp. 10351-10353.
A European Patent Office Communication along with an extended search report issued in the corresponding European Patent Application No. 12850047.7 on Jun. 11, 2015.
Bone et al., "American College of Chest Physicians/Society of Critical Care Medicine Consensus Conference: Definitions for sepsis . . . ", Critical Care Medicine, vol. 20, No. 6, Jun. 1, 1992, pp. 864-874, XP008036965A.
Koga et al., "Successful treatment of sepsis-induced disseminated intravascular coagulation in a patient with idiopathic thrombocytopenic purpura using recombinant human soluble thrombomodulin", Rheumatol Int., vol. 31, No. 12, Jan. 15, 2011, pp. 1657-1659, XP19980006A.
Wittebole et al., "Adjunctive therapies for severe sepsis", International Journal of Antimicrobial Agents, vol. 32, Nov. 1, 2008, pp. S34-S38, XP25560112A.
Bone et al., "Definitions for Sepsis and Organ Failure and Guidelines for the Use of Innovative Therapies in Sepsis," Chest (1992), vol. 101, pp. 1644-1655.
Official Action issued Aug. 17, 2015, in Russian Patent Application No. 2014124171, with English translation.
Patent Examination Report No. 2 issued Aug. 19, 2015, in Australian Patent Application No. 2012337838.
Second Office Action issued Sep. 22, 2015, in Chinese Patent Application No. 201280055832.2, with English translation.
Van Geest-Daalderop et al., "Age and First INR After Initiation of Oral Anticoagulant Therapy with Acenocoumarol Predict the Maintenance Dosage," Journal of Thrombosis and Thrombolysis (2003), vol. 15, No. 3 pp. 197-203.
Dellacroce, H., "Surviving sepsis: The role of the nurse," Modern Medicine Network (2009).
Final Rejection mailed Nov. 17, 2015, in Japanese Patent Application No. 2013-544281, with English translation.
Martin et al. "Surviving Sepsis: Initial Recognition and Resuscitation," American Association of Critical Care Nurses (2010), pp. 1-3.
Office Action issued Nov. 13, 2015, in Korean Patent Application No. 10-2014-7016082, with English translation.
Patent Examination Report No. 3 issued Nov. 19, 2015, in Australian Patent Application No. 2012337838.
U.S. Appl. No. 14/283,976, filed May 21, 2014.

MEDICAMENT FOR THERAPEUTIC TREATMENT AND/OR IMPROVEMENT OF SEPSIS

CROSS REFERENCE TO RELATED APPLICATIONS

This non-provisional application is a National Stage entry under U.S.C. §371 of International Application No. PCT/JP2012/079449 filed on Nov. 14, 2012, which claims the benefit of U.S. Provisional Application No. 61/559,864 filed on Nov. 15, 2011.

TECHNICAL FIELD

The present invention relates to a medicament for therapeutic treatment and/or improvement of sepsis in a severe septic patient.

BACKGROUND ART

Sepsis is a systemic inflammatory response syndrome (SIRS) induced by infection. Specifically, sepsis is defined as a pathological condition that meets, in addition to the presence of infection, two or more of the SIRS items ((1) body temperature>38° C. or <36° C., (2) heart rate>90/minute, (3) respiration rate>20/minute, or $PaCO_2$<32 torr, and (4) leucocyte count>12,000/μL or <4000/μL, or immature leucocytes>10%). Although presence of bacteria in blood (bacteremia) has been significantly focused so far, bacteria-positive result of blood culture is not necessarily required according to the above definition. Among sepsis, a condition presenting organ dysfunction, organ hypoperfusion, or hypotension is called severe sepsis. The organ hypoperfusion or abnormal perfusion includes lactic acidosis, oliguria, mental clouding, and the like. Among the severe sepsis, a condition continuously presenting hypotension despite of sufficient load of fluid therapy is called septic shock (Non-patent document 1). It is considered that the circulatory failure observed in these pathological conditions is caused by malfunction of the sympathetic nervous system or a mediator released from neutrophiles and the like, and the organ dysfunction is caused by tissue hypoxia (dysoxia).

Thrombomodulin has been known as a substance that acts to specifically bind to thrombin so as to inhibit the blood coagulation activity of thrombin, and at the same time, exerts anticoagulant activity so as to significantly promote the ability of thrombin to activate Protein C. It has also been known that thrombomodulin exerts to prolong the clotting time by thrombin, or suppresses platelet aggregation by thrombin. Protein C is a vitamin K-dependent protein that plays an important role in a blood coagulation and fibrinolysis, and activated by the action of thrombin to be converted as activated Protein C. It has been known that the activated Protein C inactivates activated blood coagulation factor V and activated blood coagulation factor VIII in vivo, and is involved in generation of a plasminogen activator having thrombolytic action (Non-patent document 2). Accordingly, it has been considered that thrombomodulin promotes the activation of Protein C by thrombin, and therefore is useful as an anticoagulant or a thrombolytic agent. It has also been reported that, in an animal experiment, thrombomodulin is effective for therapy or prophylaxis of diseases associated with hypercoagulable state (Non-patent document 3).

Thrombomodulin was first discovered and obtained as a glycoprotein expressed on the vascular endothelial cells of various animal species including humans, and then successfully cloned. Specifically, a gene of a human thrombomodulin precursor including a signal peptide was cloned from a human lung cDNA library by genetic engineering techniques and the entire gene sequence of thrombomodulin was analyzed, and as a result, an amino acid sequence consisting of 575 residues containing a signal peptide (in general, 18 amino acid residues are exemplified) was revealed (Patent document 1). It is known that a mature thrombomodulin, from which the signal peptide is cleaved, is composed of 5 regions, namely, an N-terminal region (amino acid residues 1 to 226, these positions are defined under an assumption that the signal peptide consists of 18 amino acid residues, and the same shall apply to the following descriptions), a region having six EGF-like structures (amino acid residues 227 to 462), an O-linked glycosylation region (amino acid residues 463 to 498), a transmembrane region (amino acid residues 499 to 521), and an cytoplasmic region (amino acid residues 522 to 557), from the N-terminal side of the mature peptide. It is also known that a partial protein having the same activity as that of the entire length thrombomodulin (i.e., a minimal active unit) is mainly consisting of the 4th, 5th, and 6th EGF-like structures from the N-terminal side in the region having six EGF-like structures (Non-patent document 4).

The entire length thrombomodulin is hardly dissolved in the absence of a surfactant, and addition of a surfactant is essential for manufacturing an entire thrombomodulin preparation. A soluble thrombomodulin is also available that can be fully dissolved even in the absence of a surfactant. The soluble thrombomodulin may be prepared by removing at least a part of the transmembrane region or the entire transmembrane region. For example, it has been confirmed that a soluble thrombomodulin consisting of only 3 regions, namely, the N-terminal region, the region having six EGF-like structures, and the O-linked glycosylation region (i.e., a soluble thrombomodulin having an amino acid sequence consisting of amino acid residues 19 to 516 of SEQ ID NO: 9) can be obtained by applying recombination techniques, and that the resulting recombinant soluble thrombomodulin has the same activity as that of an entire thrombomodulin (Patent document 1). Some other reports are also available regarding soluble thrombomodulins (Patent documents 2 to 9). A human urine-derived soluble thrombomodulin and the like are also exemplified as native thrombomodulins (Patent documents 10 and 11).

As recognized in many cases, as a result of spontaneous mutations or mutations occurring at the time of obtainment, polymorphic mutations have been found in the human genes. At present, thrombomodulin proteins in which the amino acid at the position 473 of human thrombomodulin precursor having the amino acid sequence consisting of 575 amino acid residues is converted to Val or Ala have been identified. In the nucleotide sequence encoding the amino acid sequence, this variation of amino acid residue corresponds to mutation to T or C at the position 1418 (Non-patent document 5). However, the two types of thrombomodulins are completely identical in terms of their activity and physicochemical properties, and it can be considered that they are substantially identical.

It has been reported that thrombomodulin is effective for a therapeutic treatment of disseminated intravascular coagulation (henceforth also referred to as DIC) (Non-patent document 6). As for use of thrombomodulin, in addition to the aforementioned use, thrombomodulin is expected to be used in therapeutic and prophylactic treatments of various diseases such as acute coronary syndrome (ACS), thrombosis, peripheral vessel obstruction, obstructive arteriosclerosis, vasculitis, functional disorder occurring after heart surgery, complication caused by organ transplantation, angina pectoris, transient ischemic attack, toxemia of pregnancy, diabetes, liver VOD (liver veno-occlusive disease, e.g., fulminant hepatitis, veno occlusive disease of liver occurring after bone marrow transplantation), and deep venous thrombosis (DVT), and further, sepsis and adult respiratory distress syndrome (ARDS) (Patent document 12).

PRIOR ART REFERENCES

Patent Documents

Patent document 1: Japanese Patent Unexamined Publication (Kokai) No. 64-6219
Patent document 2: Japanese Patent Unexamined Publication No. 5-213998
Patent document 3: Japanese Patent Unexamined Publication No. 2-255699
Patent document 4: Japanese Patent Unexamined Publication No. 3-133380
Patent document 5: Japanese Patent Unexamined Publication No. 3-259084
Patent document 6: Japanese Patent Unexamined Publication No. 4-210700
Patent document 7: WO92/00325
Patent document 8: WO92/03149
Patent document 9: WO93/15755
Patent document 10: Japanese Patent Unexamined Publication No. 3-86900
Patent document 11: Japanese Patent Unexamined Publication No. 3-218399
Patent document 12: WO03/061687

Non-Patent Documents

Non-patent document 1: American College of Chest Physicians, CHEST/101/6-/JUNE, 1992:1481-1483
Non-patent document 2: Koji Suzuki, Igaku no Ayumi (Progress of Medicine), Vol. 125, 901 (1983)
Non-patent document 3: K. Gomi et al., Blood, 75, 1396-1399 (1990)
Non-patent document 4: M. Zushi et al., J. Biol. Chem., 246, 10351-10353 (1989)
Non-patent document 5: D. Z. Wen et al., Biochemistry, 26, 4350-4357 (1987)
Non-patent document 6: S. M. Bates et al., Br. J. Pharmacol., 144, 1017-1028 (2005)

SUMMARY OF THE INVENTION

Object to be Achieved by the Invention

An object of the present invention is to provide a medicament or method for effective therapeutic treatment or improvement of sepsis in a severe septic patient.

Means for Achieving the Objects

International Normalized Ratio (henceforth also abbreviated as "INR") in a plasma specimen of a patient with sepsis is known to mean coagulopathy. For example, in Congress of Critical Care Medicine (CCM) held in 2003, INR>1.5 is reported as well as aPPT>60 seconds as criteria of coagulopathy (Crit. Care Med., 31, pp. 1250-1256 (2003)). However, the value of INR has not yet been authorized as a clear criterion, because the value has not been verified through clinical trials and the like. Actually, through Phase III clinical trial for treatment of patients with severe sepsis, Tifagofin as a tissue factor pathway inhibitor in a class of anticoagulants is reported to have achieved more favorable result in a group of patients with INR≤1.2 than a group of patients with INR>1.2 as a result of clinical test in which patients with INR>1.2 were mainly targeted (JAMA, July 9, Vo. 290, No. 2, pp. 238-247 (2003)). Whilst as another result of the aforementioned clinical test, among the class of patients with INR>1.2, the drug is reported to have achieved higher effect in patients with INR>1.5 than in patients with INR>1.2. Further, with Xigris, which is the only drug that has been verified to be effective against sepsis through clinical study, prolongation of prothrombin-time (PT) was observed in most of the patients in the study (93.4%).

As explained above, in the therapeutic treatment of patients with sepsis by an anticoagulant, high efficacy is expected by choosing a class of patients accompanied with coagulopathy in view of some of the clinical study results. However, it is considered that the definition of coagulopathy has not yet been authorized, because, for example, clinical results to the contrary were also obtained. In other words, how an excellent result can be obtained by choosing target patients by means of the INR value has not been clarified, and there is no common technical knowledge that what level of the INR value of a patient with sepsis assures particular effectiveness of the drug. With regard to correlation of the INR value with clinical effectiveness, it is considered that only a limited part of the correlation has been known as case-by-case basis as for some of individual drugs.

Under the circumstances, the inventors devoted their attention to thrombomodulin among anticoagulants, and conducted various researches on therapeutic and/or improving effect against sepsis. As a result, they unexpectedly found that sepsis can be therapeutically treated and/or improved more effectively in severe septic patients with one or more organ dysfunctions (except severe septic patient with organ dysfunction limited to the liver or kidney) than in severe septic patients without organ dysfunction when the INR value of the patients is more than 1.4, in other words, as for therapeutic treatment and/or improvement of sepsis by thrombomodulin, the inventors found that there is a particular correlation between severe septic patients with one or more organ dysfunctions, among the class of septic patients, and the INR value more than 1.4, which is unexpected by one of ordinary skill in the art. Further surprisingly, the inventors found that, for severe septic patients with the INR value more than 1.4 and equal to or less than 1.6, particularly remarkable effect was achieved in that a difference in mortality rate between thrombomodulin group and placebo group was higher than 15%, and as a result, they accomplished the present invention. In view of the difference in mortality rate of about 6% between drug group and placebo group achieved by Xigris (N. Engl. J. Med., 344, No. 10, March 8, pp. 699-709 (2001)), which is a sole commercially available drug in Europe for treatment of sepsis, the value of 15% as the difference in mortality rate is a remarkable value as high as about 2.5-fold, and therefore, it can be recognized that one of embodiments of the present invention achieves unexpectedly surprising effect.

Specifically, the present invention includes the followings:
[A1] A medicament for therapeutic treatment and/or improvement of sepsis which comprises thrombomodulin as an active ingredient, wherein said medicament is to administer to a patient with severe sepsis accompanied with one or more organ dysfunctions, wherein a value of International Normalized Ratio (INR) of a plasma specimen obtained from said patient is more than 1.4.

[A1-2] A medicament for therapeutic treatment and/or improvement of sepsis accompanied with coagulopathy which comprises thrombomodulin as an active ingredient, wherein said medicament is to administer to a patient with severe sepsis accompanied with one or more organ dysfunctions, wherein a value of International Normalized Ratio (INR) of a plasma specimen obtained from said patient is more than 1.4.

[A2] The medicament according to [A1] or [A1-2] mentioned above, wherein said medicament is to administer to a patient with severe sepsis accompanied with one or more organ dysfunctions, wherein a value of International Normalized Ratio (INR) of a plasma specimen obtained from said patient is more than 1.4 and equal to or less than 1.6.

[A3] The medicament according to any one of [A1] to [A2] mentioned above, wherein the patient with severe sepsis is a severe septic patient who is not a septic patient with organ dysfunction limited to the liver or kidney.

When the referred item numbers are indicated with such a range as "[A1] to [A2]" mentioned above, and the range includes an item indicated with a number having a subnumber such as [A1-2], it is meant that the item indicated with the number having a subnumber such as [A1-2] is also cited. The same shall apply to the following definitions.

[A4] The medicament according to any one of [A1] to [A3] mentioned above, wherein said medicament is to administer to a patient with severe sepsis accompanied with one or more organ dysfunctions selected from the group consisting of liver dysfunction, kidney dysfunction, respiratory organ dysfunction, and circulatory organ dysfunction.

[A5] The medicament according to any one of [A1] to [A4] mentioned above, wherein the thrombomodulin is a soluble thrombomodulin.

[A5-2] The medicament according to any one of [A1] to [A5] mentioned above, wherein the soluble thrombomodulin has the following properties (1) to (4):
(1) an action of selectively binding to thrombin,
(2) an action of promoting activation of Protein C by thrombin,
(3) an action of extending thrombin clotting time, and
(4) an action of suppressing platelet aggregation caused by thrombin.

[A5-3] The medicament according to any one of [A1] to [A5] mentioned above, wherein the soluble thrombomodulin has the following properties (1) to (5):
(1) an action of selectively binding to thrombin,
(2) an action of promoting activation of Protein C by thrombin,
(3) an action of extending thrombin clotting time,
(4) an action of suppressing platelet aggregation caused by thrombin, and
(5) anti-inflammatory action.

[A6] The medicament according to any one of [A1] to [A5-3] mentioned above, wherein the thrombomodulin is a peptide obtainable from a transformed cell prepared by transfecting a host cell with a DNA coding for the amino acid sequence of SEQ ID NO: 9 or SEQ ID NO: 11.

[A7] The medicament according to any one of [A1] to [A6] mentioned above, wherein the soluble thrombomodulin is a peptide containing the amino acid sequence of (i-1) or (i-2) mentioned below, and said peptide is a peptide having the thrombomodulin activities;
(i-1) the amino acid sequence of the positions 19 to 516 in the amino acid sequence of SEQ ID NO: 9 or 11, or
(i-2) the amino acid sequence of (i-1) mentioned above, further including substitution, deletion or addition of one or more amino acid residues.

[A7-2] The medicament according to any one of [A1] to [A6] mentioned above, wherein the soluble thrombomodulin is a peptide containing:
(i) the amino acid sequence of the positions 367 to 480 in the amino acid sequence of SEQ ID NO: 9 or 11, and the amino acid sequence of (ii-1) or (ii-2) mentioned below, and said peptide is a peptide having the thrombomodulin activities:
(ii-1) the amino acid sequence of the positions 19 to 244 in the amino acid sequence of SEQ ID NO: 9 or 11, or
(ii-2) the amino acid sequence of (ii-1) mentioned above, further including substitution, deletion or addition of one or more amino acid residues,

[A8] The medicament according to any one of [A1] to [A7-2] mentioned above, wherein the thrombomodulin is administered at a dose of 0.005 to 1 mg/kg within 5 minutes by intravenous bolus administration.

[B1] A method for therapeutic treatment and/or improvement of sepsis, which comprises the step of administrating thrombomodulin to a patient with severe sepsis, wherein a value of International Normalized Ratio (INR) of a plasma specimen obtained from said patient is more than 1.4.

[B1-2] A method for therapeutic treatment and/or improvement of sepsis accompanied with coagulopathy, which comprises the step of administrating thrombomodulin to a patient with severe sepsis, wherein a value of International Normalized Ratio (INR) of a plasma specimen obtained from said patient is more than 1.4.

[B-2] The method according to [B1] or [B1-2] mentioned above, which comprises the step of administrating thrombomodulin to a patient with severe sepsis accompanied with one or more organ dysfunctions, wherein a value of International Normalized Ratio (INR) of a plasma specimen obtained from said patient is more than 1.4 and equal to or less than 1.6.

[B3] The method according to any one of [B1] to [B-2] mentioned above, wherein the patient with severe sepsis is a severe septic patient who is not a septic patient with organ dysfunction limited to the liver or kidney.

[B4] The method according to any one of [B1] to [B3] mentioned above, which comprises the step of administrating thrombomodulin to a patient with severe sepsis accompanied with one or more organ dysfunctions selected from the group consisting of liver dysfunction, kidney dysfunction, respiratory organ dysfunction, and circulatory organ dysfunction.

[B5] The method according to any one of [B1] to [B4] mentioned above, wherein the thrombomodulin is a soluble thrombomodulin.

[B6] The method according to any one of [B1] to [B5] mentioned above, wherein the thrombomodulin is a peptide obtainable from a transformed cell prepared by transfecting a host cell with a DNA coding for the amino acid sequence of SEQ ID NO: 9 or SEQ ID NO: 11.

[B7] The method according to any one of [B1] to [B6] mentioned above, wherein the soluble thrombomodulin is a peptide containing the amino acid sequence of (i-1) or (i-2) mentioned below, and said peptide is a peptide having the thrombomodulin activities; (i-1) the amino acid sequence of the positions 19 to 516 in the amino acid sequence of SEQ ID NO: 9 or 11, or
(i-2) the amino acid sequence of (i-1) mentioned above, further including substitution, deletion or addition of one or more amino acid residues.

[B8] The method according to any one of [B1] to [B7] mentioned above, wherein the thrombomodulin is administered at a dose of 0.005 to 1 mg/kg within 5 minutes by intravenous bolus administration.

[B8-2] The method according to any one of [B1] to [B8] mentioned above, wherein the thrombomodulin is a thrombomodulin having the characteristic features mentioned in [A5-2], [A5-3] or [A7-2] mentioned above.

[B9] Use of thrombomodulin as a medicament for therapeutic treatment and/or improvement of sepsis, wherein said medicament is to administer to a patient with severe sepsis accompanied with one or more organ dysfunctions, wherein a value of International Normalized Ratio (INR) of a plasma specimen obtained from said patient is more than 1.4.

[B9-2] The use according to [B9] mentioned above, wherein the thrombomodulin is a thrombomodulin having the characteristic features mentioned in [A5-2], [A5-3] or [A7-2] mentioned above.

[B9-3] The use according to [B9] mentioned above, which has the characteristic features mentioned in any one of [A1] to [A8] mentioned above.

[C1] A medicament for therapeutic treatment and/or improvement of disseminated intravascular coagulation, wherein said medicament is to administer to a patient with disseminated intravascular coagulation accompanied with one or more organ dysfunctions, wherein a value of International Normalized Ratio (INR) of a plasma specimen obtained from said patient is higher than 1.4.

[C2] The medicament according to [C1] mentioned above, which has the characteristic features mentioned in any one of [A1] to [A8] mentioned above.

Effect of the Invention

With the medicament of the present invention containing thrombomodulin, sepsis in a severe septic patient, wherein a value of International Normalized Ratio (INR) of a plasma specimen obtained from said patient is more than 1.4, can be effectively treated and/or improved.

MODES FOR CARRYING OUT THE INVENTION

Hereafter, several preferred embodiments of the present invention (preferred modes for carrying out the invention, henceforth also referred to as "embodiments" in the specification) will be specifically explained. However, the scope of the present invention is not limited to the specific embodiments explained below.

The thrombomodulin of this embodiment preferably is known to have an action of (1) selectively binding to thrombin (2) to promote activation of Protein C by thrombin. In addition, it is preferred that the thrombomodulin is confirmed to generally have (3) an action of extending thrombin clotting time, (4) an action of suppressing platelet aggregation caused by thrombin, and/or (5) anti-inflammatory action. Such actions possessed by thrombomodulin may be referred to as thrombomodulin activities.

As the thrombomodulin activities, thrombomodulin preferably has the actions of (1) and (2) mentioned above, and more preferably has the actions of (1) to (4) mentioned above. As the thrombomodulin activities, thrombomodulin more preferably has all of the actions of (1) to (5) mentioned above.

The action of thrombomodulin to bind with thrombin can be confirmed by the study methods described in various known publications such as Thrombosis and Haemostasis, 70(3):418-422 (1993) and The Journal of Biological Chemistry, 264, 9, pp. 4872-4876 (1989). As for the action of promoting activation of Protein C by thrombin, degree of the activity of promoting the activation of Protein C by thrombin or presence or absence of the action can be easily confirmed by the study methods clearly described in various known publications including, for example, Japanese Patent Unexamined Publication No. 64-6219. Further, the action of extending thrombin clotting time, and/or the action of suppressing platelet aggregation caused by thrombin can be similarly and easily confirmed. Furthermore, the anti-inflammatory action can also be confirmed by the study methods described in various known publications including, for example, Blood, 112:3361-3670 (2008) and The Journal of Clinical Investigation, 115, 5:1267-1274 (2005).

The thrombomodulin used for the present invention is not particularly limited so far as having the thrombomodulin activities. The thrombomodulin is preferably a soluble thrombomodulin under the condition without surfactants. The solubility of the soluble thrombomodulin in water such as distilled water used for injection (in the absence of a surfactant such as Triton X-100 or polidocanol, and generally around the neutral pH range) is preferably, for example, 1 mg/mL or more or 10 mg/mL or more; preferably 15 mg/mL or more or 17 mg/mL or more; more preferably 20 mg/mL or more, 25 mg/mL or more, or 30 mg/mL or more; particularly preferably 60 mg/mL or more. In some cases, the solubility is, for example, 80 mg/mL or more, or 100 mg/mL or more. For determining whether or not a soluble thrombomodulin is successfully dissolved in water, it is understood that clear appearance of a solution and the absence of apparently observable insoluble substances is served as simple criteria, after the soluble thrombomodulin is dissolved in water and the solution is observed by visual inspection, for example, just under a white light at a position corresponding to an illumination of approximately 1000 luxes. It is also possible to observe the presence or absence of any residue after filtration.

The molecular weight of the thrombomodulin is not limited so far that it has the thrombomodulin activities as described above. The molecular weight is preferably 100,000 or smaller, more preferably 90,000 or smaller, still more preferably 80,000 or smaller, most preferably 70,000 or smaller, and the molecular weight is preferably 50,000 or larger, most preferably 60,000 or larger. The molecular weight of the soluble thrombomodulin can be easily measured by ordinary methods for measuring molecular weight of protein. Measurement by mass spectrometry is preferred, and MALDI-TOF-MS method is more preferred. For obtaining soluble thrombomodulin having a molecular weight within a desired range, a soluble thrombomodulin, which is obtained by culturing a transformant cell prepared by transfecting a host cell with a DNA encoding soluble thrombomodulin using a vector, can be subjected to fractionation using column chromatography or the like as described later.

The thrombomodulin used for the present invention preferably comprises the amino acid sequence consisting of the amino acid residues at the positions 19 to 132 of SEQ ID NO: 1, which has been known as the central portion of the thrombomodulin activities of human thrombomodulin, and the thrombomodulin is not particularly limited, so long as the thrombomodulin comprises the amino acid sequence consisting of the amino acid residues at the positions 19 to 132 of SEQ ID NO: 1. The amino acid sequence consisting of the amino acid residues at the positions 19 to 132 of SEQ ID NO: 1 may be naturally or artificially mutated, so long as the sequence has an action to promote the activation of Protein C by thrombin, namely, one of the thrombomodulin activities. Specifically, the sequence may comprise substitution, deletion, or addition of one or more amino acid residue in the amino acid sequence consisting of the amino acid residues at the positions 19 to 132 of SEQ ID NO: 1. Acceptable level of the mutation is not particularly limited, so long as the amino acid sequence has the thrombomodulin activities. An example includes a homology 50% or more as amino acid sequences, and the homology is preferably 70% or more, more preferably 80% or more, further preferably 90% or more, particularly preferably 95% or more, and most preferably 98% or more. Such mutated amino acid sequence including substitution, deletion or addition of one or more amino acid residues is referred to as homologous mutation sequence. As described later, these mutated amino acid sequences can be easily produced by using ordinary gene manipulation techniques. The thrombomodulin is not particularly limited so far that it has the aforementioned sequence and the action of selectively binding to thrombin to promote activation of Protein C by thrombin at least as the whole thrombomodulin, but the thrombomodulin preferably also has the anti-inflammatory action.

The amino acid sequence of SEQ ID NO: 3 comprises the mutation of Val as the amino acid at the position 125 of the sequence of SEQ ID NO: 1 to Ala. The thrombomodulin used for the present invention also preferably comprises the amino acid sequence from the position 19 to 132 of SEQ ID NO: 3.

As described above, although the thrombomodulin used for the present invention is not particularly limited so long that the thrombomodulin has at least the amino acid sequence from the position 19 to 132 of SEQ ID NO: 1 or 3, or a homologous mutation sequence thereof, and comprises at least a peptide sequence having the thrombomodulin activities, preferred examples of the thrombomodulin include a peptide consisting of the sequence from the position 19 to 132 or 17 to 132 in either of SEQ ID NO: 1 or SEQ ID NO: 3, and a peptide consisting of a homologous mutation sequence of the aforementioned sequence and having at least the thrombomodulin activities. A peptide consisting of the sequence from the position 19 to 132 in either of SEQ ID NO: 1 or SEQ ID NO: 3 is more preferred. In another embodiment, a peptide consisting of a homologous mutation sequence of the sequence from the position 19 to 132 or 17 to 132 in either of SEQ ID NO: 1 or SEQ ID NO: 3 and having at least the thrombomodulin activities is more preferred.

As another embodiment of the thrombomodulin according to the present invention, the thrombomodulin preferably comprises the amino acid sequence from the positions 19 to 480 of SEQ ID NO: 5, which is not particularly limited so long as the thrombomodulin comprises the amino acid sequence from the position 19 to 480 of SEQ ID NO: 5. The amino acid sequence from the positions 19 to 480 of SEQ ID NO: 5 may be a homologous mutation sequence thereof, so long as the sequence has an action to promote the activation of Protein C by thrombin, i.e., one of the thrombomodulin activities.

The sequence of SEQ ID NO: 7 comprises the mutation of Val as the amino acid at the position 473 of the sequence of SEQ ID NO: 5 to Ala. The thrombomodulin used for the present invention also preferably comprises the amino acid sequence from the position 19 to 480 of SEQ ID NO: 7.

As described above, although the thrombomodulin used for the present invention is not particularly limited so long as the thrombomodulin has at least the sequence from the position 19 to 480 in either of SEQ ID NO: 5 or SEQ ID NO: 7, or a homologous mutation sequence thereof, and comprises at least a peptide sequence having the thrombomodulin activities, preferred examples of the thrombomodulin include a peptide consisting of the sequence from the position 19 to 480 or 17 to 480 in either of SEQ ID NO: 5 or SEQ ID NO: 7, and a peptide consisting of a homologous mutation sequence of the aforementioned sequence and having at least the thrombomodulin activities. A peptide consisting of the sequence from the position 19 to 480 of SEQ ID NO: 5 or 7 is more preferred. In another embodiment, a peptide consisting of a homologous mutation sequence of the sequence from the position 19 to 480 or 17 to 480 in either of SEQ ID NO: 5 or SEQ ID NO: 7, and having the thrombomodulin activities is more preferred.

As another embodiment of the thrombomodulin according to the present invention, the thrombomodulin preferably comprises the amino acid sequence from the position 19 to 515 of SEQ ID NO: 9, which is not particularly limited so long as the thrombomodulin comprises the amino acid sequence from the position 19 to 515 of SEQ ID NO: 9. The amino acid sequence from the position 19 to 515 of SEQ ID NO: 9 may be a homologous mutation sequence thereof, so long as the sequence has an action to promote the activation of Protein C by thrombin, i.e., the thrombomodulin activities.

The amino acid sequence of SEQ ID NO: 11 comprises the mutation of Val as the amino acid at the position 473 of SEQ ID NO: 9 to Ala. The thrombomodulin used for the present invention also preferably comprises the amino acid sequence from the position 19 to 515 of SEQ ID NO: 11.

As described above, although the thrombomodulin used for the present invention is not particularly limited so long as the thrombomodulin has at least the sequence from the position 19 to 515 in either of SEQ ID NO: 9 or SEQ ID NO: 11, or a homologous mutation sequence thereof, and comprises a peptide sequence having at least the thrombomodulin activities, more preferred examples include a peptide having the sequence from position 19 to 516, 19 to 515, 17 to 516, or 17 to 515 in either of SEQ ID NO: 9 or SEQ ID NO: 11, and a peptide consisting of a homologous mutation sequence of the aforementioned sequence and having at least the thrombomodulin activities. A peptide having the sequence from the position 19 to 516, 19 to 515, 17 to 516, or 17 to 515 of SEQ ID NO: 9 is particularly preferred. A mixture thereof is also a preferred example. In another embodiment, a peptide having the sequence from the position 19 to 516, 19 to 515, 17 to 516, or 17 to 515 of SEQ ID NO: 11 is particularly preferred. A mixture thereof is also a preferred example. Further, a peptide consisting of a homologous mutation sequence thereof and having at least the thrombomodulin activities is also a preferred example. It is preferred that the soluble thrombomodulin also has the anti-inflammatory action.

A peptide having a homologous mutation sequence is as described above, and means a peptide that may comprise substitution, deletion, or addition of at least one, namely, one or more, preferably several (for example, 1 to 20, preferably 1 to 10, more preferably 1 to 5, particularly preferably 1 to 3) amino acid residues, in the amino acid sequence of the subjected peptide. Although acceptable level of mutation is not particularly limited so long as the peptide has the thrombomodulin activities, an example of the acceptable level of homology includes 50% or more as an amino acid sequences, and the homology may be preferably 70% or more, more preferably 80% or more, further preferably 90% or more, particularly preferably 95% or more, and most preferably 98% or more.

Preferred examples of the thrombomodulin used for the present invention also include the peptide consisting of the sequence of SEQ ID NO: 14 (462 amino acid residues), the peptide consisting of the sequence of SEQ ID NO: 8 (272 amino acid residues), and the peptide consisting of the sequence of SEQ ID NO: 6 (236 amino acid residues) described in Japanese Patent Unexamined Publication No. 64-6219.

The thrombomodulin used for the present invention is not particularly limited so long as the thrombomodulin has at least the amino acid sequence from the position 19 to 132 in either of SEQ ID NO: 1 or SEQ ID NO: 3. As such a thrombomodulin, a peptide having at least the amino acid sequence from the position 19 to 480 in either of SEQ ID NO: 5 or SEQ ID NO: 7 is preferred, and a peptide having at least the amino acid sequence from the position 19 to 515 in either of SEQ ID NO: 9 or SEQ ID NO: 11 is more preferred. A more preferred example of the peptide having at least the amino acid sequence from the position 19 to 515 in either of SEQ ID NO: 9 or SEQ ID NO: 11 is a peptide having the sequence from the position 19 to 516, 19 to 515, 19 to 514, 17 to 516, 17 to 515, or 19 to 514 in either of SEQ ID NO: 9 or SEQ ID NO: 11. Furthermore, a mixture of peptides each consisting of the sequence from the position 19 to 516, 19 to 515, 19 to 514, 17 to 516, 17 to 515, or 19 to 514 in either of SEQ ID NO: 9 or SEQ ID NO: 11 is also a preferred example.

In the case of the aforementioned mixture, the mixing ratio of a peptide that starts from the position 17 and a peptide that starts from the position 19 for each of SEQ ID NOS: 9 and 11 is, for example, 30:70 to 50:50, preferably 35:65 to 45:55.

Further, the mixing ratio of a peptide that terminates at the position 514, a peptide that terminates at the position 515, and a peptide that terminates at the position 516 for each of SEQ ID NOS: 9 and 11 is, for example, 0:0:100 to 0:90:10, or 0:70:30 to 10:90:0, or 10:0:90 to 20:10:70, if desired.

The mixing ratio of the peptides can be determined by an ordinary method.

The sequence of the positions 19 to 132 in SEQ ID NO: 1 corresponds to the sequence of the positions 367 to 480 in SEQ ID NO: 9, and the sequence of the positions 19 to 480 in SEQ ID NO: 5 corresponds to the sequence of the positions 19 to 480 in SEQ ID NO: 9. Further, the sequence of the positions 19 to 132 in SEQ ID NO: 3 corresponds to the sequence of the positions 367 to 480 in SEQ ID NO: 11, and the sequence of the positions 19 to 480 in SEQ ID NO: 7 corresponds to the sequence of the positions 19 to 480 in SEQ ID NO: 11. Furthermore, all the sequences of the positions 1 to 18 in SEQ ID NOS: 1, 3, 5, 7, 9 and 11 are identical sequences.

As described below, these thrombomodulins according to the present invention can be obtained from transformant cells prepared by transfecting host cells with a DNA encoding the peptide (specifically, the nucleotide sequences of SEQ ID NOS: 2, 4, 6, 8, 10, 12, and the like) by using a vector.

It is sufficient that these peptides only have the aforementioned amino acid sequences, and a sugar chain may be attached or not attached, which not particularly limited. In gene manipulation techniques, a type of a sugar chain, a position to which a sugar chain is added, and a level of addition thereof differ depending on a type of host cells used, and any techniques may be used. As for binding position of a sugar chain and a type thereof, facts described in Japanese Patent Unexamined Publication No. 11-341990 are known, and the thrombomodulins according to the present invention may be added with the same sugar chain at the same position. Two types of N-linked sugar chains, those of fucosyl biantennary type and fucosyl triantennary type, may bind to the thrombomodulin of this embodiment, and ratio thereof is, for example, 100:0 to 60:40, preferably 95:5 to 60:40, more preferably 90:10 to 70:30. The ratio of these sugar chains can be measured on a two-dimensional sugar chain map described in Biochemical Experimental Methods, Vol. 23, Methods of Researches on Glycoprotein Sugar Chains, Japan Scientific Societies Press (1990), and the like. Furthermore, when a sugar composition of the thrombomodulin of this embodiment is examined, neutral saccharides, aminosaccharides, and sialic acid are detected, of which content may be, each independently for example, 1 to 30%, preferably 2 to 20%, more preferably 5 to 10%, in terms of weight ratio based on the protein content. The sugar contents can be measured by the methods described in Lecture of New Biochemical Experiments, Vol. 3, Sugar I, Glycoprotein (Book 1), Tokyo Kagaku Dojin (1990) (neutral saccharides: phenol-sulfuric acid method, aminosaccharides: Elson-Morgan method, sialic acid:periodic acid-resorcinol method).

Although the method for obtaining thrombomodulin is not limited to obtaining it by genetic manipulation as described later, as a signal sequence that can be used for expression where the thrombomodulin is obtained by gene manipulation, a nucleotide sequence encoding the amino acid sequence of the positions 1 to 18 in SEQ ID NO: 9, and a nucleotide sequence encoding the amino acid sequence of the positions 1 to 16 in SEQ ID NO: 9 can be used, and other known signal sequences such as the signal sequence of human tissue plasminogen activator can also be used (International Publication WO88/9811).

When a DNA sequence encoding thrombomodulin is introduced into a host cell, examples of preferred methods include a method of incorporating a DNA sequence encoding thrombomodulin into, preferably, a vector, more preferably an expression vector capable of being expressed in animal cells, and then introducing the DNA with the vector. An expression vector is a DNA molecule that is constituted with a promoter sequence, a sequence for adding a ribosome binding site to mRNA, a DNA sequence encoding a protein to be expressed, a splicing signal, a terminator sequence for transcription termination, a replication origin sequence, and the like. Examples of preferred animal cell expression vector include pSV2-X reported by Mulligan R. C. et al. (Proc. Natl. Acad. Sci. U.S.A., 78, 2072 (1981)); pBP69T (69-6) reported by Howley P. M. et al. (Methods in Emzymology, 101, 387 (1983), Academic Press), and the like. Further, there is also another preferred embodiment in which DNA is introduced into an expression vector expressible in a microorganism.

Examples of host cell that can be used in production of such peptides as mentioned above include animal cells. Examples of the animal cells include Chinese hamster ovary (CHO) cells, COS-1 cells, COS-7 cells, VERO (ATCC CCL-81) cells, BHK cells, canine kidney-derived MDCK cells, hamster AV-12-664 cells, and the like. In addition, examples of host cell derived from human include HeLa cells, WI38 cells, human 293 cells, and PER.C6 cells. Of these cells, CHO cells are very common and preferred, and among the CHO cells, dihydrofolate reductase (DHFR)-deficient CHO cells are more preferred.

In a gene manipulation process or a peptide production process, microorganisms such as *Escherichia coli* are also often used. A host-vector system suitable for each process is preferably used, and an appropriate vector system can also be selected for the aforementioned host cells. A thrombomodulin gene used in a genetic recombination technique has been cloned. Examples of production of thrombomodulin by such a gene recombination technique have been disclosed, and further, methods for purifying thrombomodulin to obtain a purified product thereof are also known (Japanese Patent Unexamined Publication Nos. 64-6219, 2-255699, 5-213998, 5-310787, 7-155176; and J. Biol. Chem., 26410351-10353 (1989)). Therefore, the thrombomodulin used for the present invention can be produced by using the methods described in the aforementioned reports, or by similar methods. For example, Japanese Patent Unexamined Publication No. 64-6219 discloses the *Escherichia coli* K-12 strain DH5 (ATCC Accession No. 67283) containing a plasmid pSV2TMJ2 that contains a DNA encoding the full-length thrombomodulin. This strain re-deposited at the former National Institute of Bioscience and Human-Technology (currently Independent Administrative Institution, National Institute of Advanced Industrial Science and Technology, International Patent Organism Depositary) (*Escherichia coli* DH5/pSV2TMJ2) (FERM BP-5570) can also be used. The thrombomodulin according to the present invention can be prepared by a known gene manipulation technique using a DNA encoding the full-length thrombomodulin as a starting material.

The thrombomodulin of this embodiment may be prepared by a conventionally known method or a similar method. For example, the aforementioned method of Yamamoto et al. (Japanese Patent Unexamined Publication No. 64-6219) or the method described in Japanese Patent Unexamined Publication No. 5-213998 can be referred to. Specifically, for example, a DNA encoding the amino acid sequence of SEQ ID NO: 9 is prepared from a human-derived thrombomodulin gene by a gene manipulation technique, and may be further modified as required. For such modification, in order to obtain a DNA encoding the amino acid sequence of SEQ ID NO: 11 (which specifically consists of the nucleotide sequence of SEQ ID NO: 12), codons encoding the amino acid at the position 473 in the amino acid sequence of SEQ ID NO: 9 (in particular, the nucleotide at the position 1418 in SEQ ID NO: 10) are mutated by site-directed mutagenesis according to the method described by Zoller M. J. et al. (Method in Enzymology, 100:468-500 (1983), Academic Press). For example, by using a synthetic DNA for mutation having the nucleotide sequence of SEQ ID NO: 13, the nucleotide T at the position 1418 in SEQ ID NO: 10 may be converted to the nucleotide C to obtain a mutated DNA.

The DNA prepared as described above is incorporated into, for example, Chinese hamster ovary (CHO) cells to obtain transformant cells. Such cells are subjected to appropriate selection, and thrombomodulin purified by a known method can be produced from a culture solution obtained by culturing a selected cell. As described above, the DNA (SEQ ID NO: 10) encoding the amino acid sequence of SEQ ID NO: 9 is preferably transfected into the aforementioned host cell.

The method for producing thrombomodulin of this embodiment is not limited to the aforementioned method. For example, it is also possible to extract and purify the thrombomodulin from urine, blood, other body fluids and the like, or extract and purify the thrombomodulin from a tissue producing thrombomodulin or a culture of the aforementioned tissue and the like. Further, the thrombomodulin may be further subjected to a cleavage treatment using a protease, as required.

For the culture of the aforementioned transformant cell, a medium used for ordinary cell culture may be used, and it is preferable to culture the transformant cell in various kinds of media in advance to choose an optimal medium. For example, a known medium such as MEM medium, DMEM medium, and 199 medium may be used as a base medium, and a further improved medium or a medium added with supplements for various media may be used. Examples of the culture method include serum culture, in which culture is performed in a medium containing blood serum, and serum-free culture, in which culture is performed in a medium not containing blood serum. Although the culture method is not particularly limited, the serum-free culture is preferred.

When serum is added to a medium in the case of the serum culture, bovine serum is preferred. Examples of bovine serum include fetal bovine serum, neonate bovine serum, calf bovine serum, adult bovine serum, and the like, and any of these examples may be used so far that the serum is suitable for the cell culture. As the serum-free medium used in the serum-free culture, commercially available media can be used. Serum-free media suitable for various cells are marketed, and for example, for the CHO cell, CD-CHO, CHO-S-SFMII and CHO-III-PFM are sold by Invitrogen, and IS CHO, IS CHO-CD medium, and the like are sold by Irvine Scientific. These media may be used without any treatment, or they may be improved or added with supplements and used. Examples of the serum-free medium further include the DMEM medium containing 5 mg/L each of insulin, transferrin, and selenious acid. As described above, the medium is not particularly limited so far that the medium can be used to produce the thrombomodulin of this embodiment. The culture method is not particularly limited, and any of batch culture, repetitive batch culture, fed-batch culture, perfusion culture, and the like may be used.

When the thrombomodulin used for the present invention is prepared by the aforementioned cell culture method, diversity may be observed in the N-terminus amino acid due to posttranslational modification of the protein. For example, the amino acid of the position 17, 18, 19 or 22 in SEQ ID NO: 9 may serve as the N-terminus amino acid. Further, for example, the N-terminus amino acid may be modified so that the glutamic acid at the position 22 is changed to pyroglutamic acid. It is preferred that the amino acid of the position 17 or 19 serves as the N-terminus amino acid, and it is more preferred that the amino acid of the position 19 serves as the N-terminus amino acid. Further, there is also another embodiment in which the amino acid of the position 17 serves as the N-terminus amino acid, which is a preferred embodiment. As for the modification, diversity and the like mentioned above, similar examples can be mentioned for the sequence of SEQ ID NO: 11.

Further, when the soluble thrombomodulin is prepared by using a DNA having the nucleotide sequence of SEQ ID NO: 10, diversity of the C-terminus amino acid may be observed, and a peptide shorter by one amino acid residue may be produced. Specifically, the C-terminus amino acid may be modified so that the amino acid of the position 515 serves as the C-terminus amino acid, and further the position 515 is amidated. Further, a peptide shorter by two amino acid residues may be produced. Specifically, the amino acid of the position 514 may serve as the C-terminus amino acid. Therefore, any of peptides having significant diversity of the N-terminus amino acid and C-terminus amino acid, or a mixture of them may be produced. It is preferred that the amino acid of the position 515 or the amino acid of the position 516 serves as the C-terminus amino acid, and it is more preferred that the amino acid of the position 516 serves as the C-terminus amino acid. Further, there is also another embodiment in which the amino acid of the position 514 serves as the C-terminus amino acid, which is a preferred embodiment. Concerning the modification, diversity and the like described above, the same shall apply to a DNA having the nucleotide sequence of SEQ ID NO: 12.

The thrombomodulin obtained by the method described above may be a mixture of peptides having diversity in the N-terminus and C-terminus amino acids. Specific examples include a mixture of peptides having the sequences of the positions 19 to 516, positions 19 to 515, positions 19 to 514, positions 17 to 516, positions 17 to 515, and positions 17 to 514 in SEQ ID NO: 9.

Then, isolation and purification of thrombomodulin from a culture supernatant or culture obtained as described above can be carried out by known methods [edited by Takeichi Horio, *Tanpakushitsu/Koso no Kiso Jikken Ho* (Fundamental Experimental Methods for Proteins and Enzymes) (1981)]. For example, it is preferable to use ion exchange chromatography or adsorption chromatography, which utilizes an interaction between thrombomodulin and a chromatographic carrier on which functional groups having a charge opposite to that of thrombomodulin are immobilized. Another preferred example is affinity chromatography utilizing specific affinity with thrombomodulin. Preferred examples of adsorbent include thrombin that is a ligand of thrombomodulin and an anti-thrombomodulin antibody. As the antibody, anti-thrombomodulin antibodies having appropriate properties or recognizing appropriate epitopes can be used. Examples include, for example, those described in Japanese Patent Publication (Kokoku) No. 5-42920, Japanese Patent Unexamined Publication Nos. 64-45398 and 6-205692 and the like. Other examples include gel filtration chromatography and ultrafiltration, which utilize the molecular size of thrombomodulin. Other examples further include hydrophobic chromatography that utilizes hydrophobic bond between a chromatographic carrier on which hydrophobic groups are immobilized, and a hydrophobic portion of thrombomodulin. Furthermore, hydroxyapatite may be used as a carrier in adsorption chromatography, of which examples include, for example, those described in Japanese Patent Unexamined Publication No. 9-110900. These means may be used in combination, as required. Although degree of purification can be selected depending on a purpose of use and the like, it is desirable to purify thrombomodulin until a single band is obtained as a result of electrophoresis, preferably SDS-PAGE, or a single peak is obtained as a result of gel filtration HPLC or reverse phase HPLC of the isolated and purified product. It should be understood that, when two or more types of thrombomodulins are used, it is preferred that only the bands of the thrombomodulins are substantially obtained, and it is not required to obtain one single band.

Specific examples of the purification method used in the present invention include a purification method using the thrombomodulin activities as a criterion, for example, a purification method comprising roughly purifying a culture supernatant or a culture product with an ion exchange column Q-Sepharose Fast Flow to collect a fraction having the thrombomodulin activities; then purifying the fraction with an affinity column, DIP-thrombin-agarose (diisopropylphosphorylthrombin agarose) column, as the main purification step to recover a fraction having potent thrombomodulin activities; then concentrating the recovered fraction and followed by gel filtration to obtain a thrombomodulin active fraction as a purified product (Gomi K. et al., Blood, 75: 1396-1399 (1990)). An example of the thrombomodulin activities used as the criterion is an activity of promoting the activation of Protein C by thrombin. Other preferred examples of the purification method will be exemplified below.

An appropriate ion exchange resin having good adsorptive condition for thrombomodulin is selected and purification by ion exchange chromatography is performed. A particularly preferred example is a method comprising the use of Q-Sepharose Fast Flow equilibrated with a 0.02 mol/L Tris-HCl buffer (pH 7.4) containing 0.18 mol/L NaCl. After washing as required, elution can be performed with a 0.02 mol/L Tris-HCl buffer (pH 7.4) containing 0.3 mol/L NaCl, for example, to obtain thrombomodulin as a roughly purified product.

Then, for example, a substance having specific affinity to thrombomodulin can be immobilized on a resin to perform purification by affinity chromatography. Preferred examples include a DIP-thrombin-agarose column and an anti-thrombomodulin monoclonal antibody column. In the case of the DIP-thrombin-agarose column, the column is equilibrated beforehand with a 20 mmol/L Tris-HCl buffer (pH 7.4) containing 100 mmol/L NaCl and 0.5 mmol/L calcium chloride, and the aforementioned roughly purified product is then charged on the column, washed as required, and then eluted with, for example, a 20 mmol/L Tris-HCl buffer (pH 7.4) containing 1.0 mol/L NaCl and 0.5 mmol/L calcium chloride to obtain thrombomodulin as a purified product. In the case of the anti-thrombomodulin monoclonal antibody column, an example of the method comprises: contacting an anti-thrombomodulin monoclonal antibody solution in a 0.1 mol/L NaHCO$_3$ buffer (pH 8.3) containing 0.5 mol/L NaCl with Sepharose 4FF (GE Health Care Biosciences) activated with CNBr beforehand to obtain the resin Sepharose 4FF coupled with the anti-thrombomodulin monoclonal antibodies, equilibrating the resin filled in a column beforehand with, for example, a 20 mmol/L phosphate buffer (pH 7.3) containing 0.3 mol/L NaCl, washing as required, and then performing elution with a 100 mmol/L glycine-HCl buffer (pH 3.0) containing 0.3 mol/L NaCl. An effluent may be neutralized with an appropriate buffer to obtain a product as a purified product.

Subsequently, the purified product is adjusted to pH 3.5, and then charged on a cation exchanger, preferably SP-Sepharose FF (GE Health Care Biosciences) as a strong cation exchanger, equilibrated with a 100 mmol/L glycine-HCl buffer (pH 3.5) containing 0.3 mol/L NaCl, and washing is performed with the same buffer to obtain a non-adsorptive fraction. The resulting fraction is neutralized with an appropriate buffer to obtain a highly purified product. These products are preferably concentrated by ultrafiltration.

Further, it is also preferable to exchange the buffer by gel filtration. For example, a highly purified product concentrated by ultrafiltration can be charged on a Sephacryl S-300 column or S-200 column equilibrated with a 20 mmol/L phosphate buffer (pH 7.3) containing 50 mmol/L NaCl, and then developed for fractionation with a 20 mmol/L phosphate buffer (pH 7.3) containing 50 mmol/L NaCl. The activity for promoting the activation of Protein C by thrombin can be confirmed to collect an active fraction and thereby obtain a buffer-exchanged highly purified product. In order to improve safety, a highly purified product obtained as described above is preferably filtered through an appropriate filter for eliminating viruses such as Planova 15N (Asahi Kasei Medical Co., Ltd.), and then the resultant can be concentrated by ultrafiltration to a desired concentration. Finally, the product is preferably filtered through an aseptic filtration filter.

According to the present invention, there is provided a medicament for therapeutic treatment and/or improvement of sepsis which comprises thrombomodulin as an active ingredient, wherein said medicament is to administer to a patient with severe sepsis accompanied with one or more organ dysfunctions, wherein a value of International Normalized Ratio (INR) of a plasma specimen obtained from said patient is more than 1.4.

That is, the medicament for therapeutic treatment and/or improvement of sepsis according to this embodiment is a medicament for therapeutic treatment and/or improvement of sepsis in a patient with severe sepsis accompanied with one or more organ dysfunctions, wherein a value of International Normalized Ratio (INR) of a plasma specimen obtained from said patient is more than 1.4.

There is also provided a medicament for decreasing mortality of a human patient with severe sepsis accompanied with one or more organ dysfunctions, wherein a value of International Normalized Ratio (INR) of a plasma specimen obtained from said patient is more than 1.4.

As for the therapeutic treatment and/or improvement of sepsis, examples of preferred effects thereof include, for example, "prevention of death of a patient from sepsis". Examples also include "prevention of aggravation of general conditions of a patient by sepsis".

The sepsis referred to in this embodiment is known as a severe systemic infectious disease wherein microorganisms continuously or intermittently invade into blood from an infection focus, which disease is induced by a disease such as infectious diseases, malignant tumors, hepatic cirrhosis, renal failure, diabetes, and dystocia, or a therapeutic treatment for injury or disease such as use of indwelling catheter, infusion device, dialysis, and the like and tracheostomy. If the symptoms advance, a systemic shock is induced by septic shock, i.e., rapid decrease of blood pressure and peripheral circulatory failure, and lethality is provided by organ dysfunctions of vital organs, such as lung, kidney, liver, heart, alimentary canal, and central nervous system. As a complication accompanying sepsis, there is induced adult respiratory distress syndrome (ARDS) characterized by edema of lung stroma, hemorrhage and acute respiratory failure due to lung capillary obstruction associated with DIC or activation of neutrophiles and migration and accumulation thereof in lung parenchyma, which results in extremely bad prognosis.

The sepsis referred to in this embodiment is the systemic inflammatory response syndrome (SIRS) induced by infection. More specifically, it includes a pathological condition that meets, in addition to the presence of infection, two or more of the SIRS items ((1) body temperature>38° C. or <36° C., (2) heart rate>90/minute, (3) respiration rate>20/minute, or $PaCO_2$<32 torr, and (4) leucocyte count>12,000/μL or <4000/μL, or bademia>10%), and sepsis can be basically diagnosed on the basis of such a pathological condition.

There are several methods for diagnosing sepsis, and they are summarized in Levy M. et al., Crit. Care. Med., 31:1250-1256. For example, there are a method based on diagnosis performed by a medical practitioner, and a method of using test values and the like Examples of the latter include a method in which when two items are fulfilled among the four items of (1) body temperature>38° C. or <36° C., (2) heart rate>90/minute, (3) respiration rate>20/minute, or necessity of artificial respiration, and (4) leucocyte count>12,000/μL or <4000/μL, or bandemia>10%, diagnosis of SIRS is established, and SIRS for which a microorganism is identified or suspected as the cause thereof is diagnosed as sepsis [LaRosa S., the homepage of The Cleveland Clinic]. Another method similar to the above method is described in Members of the American College of Chest Physicians/Society of Critical Care Medicine Consensus Conference: Crit. Care Med., 20, 864-874 (1992).

Examples of the symptoms of sepsis include, for example, bacteriemia, septicemia, systemic inflammatory response syndrome (SIRS), sepsis (SIRS for which a microorganism is identified or suspected as the cause thereof), severe sepsis, septic shock, intractable septic shock, and multiple organ dysfunction syndrome (henceforth also referred to as MODS) (Harrison's Principles of Internal Medicine, 15th edition of original work, Section 124, pp. 828-833, Medical Science International, Ltd.). The aforementioned conditions are exemplified as symptoms on which the medicament of the present invention for therapeutic treatment and/or improvement is effective.

Although the sepsis is not particularly limited so long as a disease is diagnosed as sepsis on the basis of the aforementioned diagnosis criteria, it is preferably sepsis accompanied by abnormal coagulation (sepsis with coagulopathy). Although the coagulopathy is not particularly limited so long as INR of a plasma specimen obtained from patient is more than 1.2, it is preferably more than 1.3, more preferably more than 1.4.

Examples of the bacteriemia include a condition that presence of bacteria in blood is verified by a positive result of blood culture.

Examples of the septicemia include a condition that presence of microorganisms or other toxins in blood is confirmed.

Examples of the systemic inflammatory response syndrome (SIRS) include a condition of a preliminary stage of DIC, as described above.

Examples of the severe sepsis include sepsis accompanied by one or more symptoms including organ dysfunction such as metabolic acidosis, organ hypoperfusion, acute encephalopathy, oliguria, hypoxemia or disseminated intravascular coagulation, and hypotension. As sepsis, one presenting organ dysfunction, organ hypoperfusion, or hypotension is called severe sepsis. The organ hypoperfusion or abnormal perfusion includes lactic acidosis, oliguria, mental clouding, and the like. Among the severe sepsis, a condition persistently presenting hypotension despite of sufficient load of fluid therapy is called as septic shock.

More specifically, the severe sepsis referred to in this embodiment is as follows.

Examples of the septic shock include a condition with hypotension (blood pressure of 90 mmHg or lower or lower than usual blood pressure by 40 mmHg or more), not responding to resuscitation by fluid replacement, and accompanied by organ failure.

Examples of the intractable septic shock include a condition with septic shock continuing over 1 hour or longer, and not responding to a hypertensor with fluid therapy.

Examples of the multiple organ dysfunction syndrome (MODS) include a condition with malfunction of one or more organs, and requiring medical intervention for maintaining homeostasis.

INR referred to in this embodiment is an examination criterion that defines blood coagulopathy. INR means a prothrombin time (henceforth also abbreviated as PT) normalized as for differences between manufacturing lots of thromboplastin preparations. INR is generally defined as follows:

INR value=(Coagulation time (sec) of test specimen/ Coagulation time (sec) of control specimen)$^{(ISI\ value)}$ In the equation, coagulation time (sec) of test specimen represents PT of test plasma specimen of a subject to be examined, and ISI represents International Sensitivity Index.

Examples of the severe sepsis referred to in this embodiment include sepsis accompanied by one or more symptoms including organ dysfunction such as metabolic acidosis, acute encephalopathy, oliguria, hypoxemia or disseminated intravascular coagulation, and hypotension, as described above. The term severe means that the disease is in a critical condition for life support. Examples of the severe sepsis include, in particular, sepsis accompanied by one or more organ dysfunctions. Although the organ dysfunction is not particularly limited so far that the organ dysfunction is induced by sepsis, the organ dysfunction preferably includes failure of an organ that is essential for supporting life. Examples of the one or more organ dysfunctions include one or more organ dysfunctions selected from the group consisting of circulatory organ dysfunction, respiratory organ dysfunction, kidney dysfunction and liver dysfunction, preferred examples include one or more organ dysfunctions selected from the group consisting of respiratory organ dysfunction, circulatory organ dysfunction, and kidney dysfunction, and more preferred examples include one or more organ dysfunctions selected from the group consisting of respiratory organ dysfunction, and circulatory organ dysfunction. Although number of the organ dysfunctions is not particularly limited so far that the number is one or more, the number may be preferably two or more. In particular, it is preferred that there are two kinds of organ dysfunctions of respiratory organ dysfunction and circulatory organ dysfunction.

The circulatory organ dysfunction is not particularly limited so long as a generally known circulatory organ dysfunction, and examples include, for example, blood pressure decrease and shock.

The respiratory organ dysfunction is not particularly limited so long as a generally known respiratory organ dysfunction, and examples include, for example, hypoxemia, acute lung injury and dyspnea.

The kidney dysfunction is not particularly limited so long as a generally known kidney dysfunction, and examples include, for example, renal function disorder, oliguria, and renal failure.

The liver dysfunction is not particularly limited so long as a generally knows liver dysfunction, and examples include, for example, hepatic function disorder, jaundice, hepatic failure, and the like.

These organ dysfunctions are generally known as described in publications published before the application date of this application, for example, Funada H., "Elucidation and Treatment Strategy for Sepsis", Iyaku Journal Co., Ltd., p. 38—(2006)), "Surviving Sepsis Campaign: international guidelines for management of severe sepsis and septic shock 2008" (Crit. Care Med., 2008 January; 36(1):296-327), and the like.

It is supposed that organ dysfunction may be induced by a factor other than sepsis, such as in the case of drug-induced organ dysfunction, and accordingly, it is desirable that patients with organ dysfunction limited to the liver or kidney are excluded from the severe septic patients. It is also known that thrombocytopenia may be developed as a result of organ dysfunction. Although platelet count in patients to be administered with the medicament of this embodiment is not particularly limited so far that the platelet count is less than 300,000/μL, the count is preferably less than 200,000 μL, more preferably less than 150,000/μL.

In this embodiment, the value of INR in a plasma specimen of a sepsis patient is not particularly limited so far that the value is more than 1.4, and when INR is more than 1.4, thrombomodulin is more effective for sepsis patients with one or more organ dysfunctions. The maximum INR may be, for example, 2.0 or lower, preferably 1.9 or lower, more preferably 1.8 or lower, still more preferably 1.7 or lower, most preferably 1.6 or lower. The value may also be preferably 1.5 or lower. It may also be preferred that a patient with an INR value of 1.7 is excluded.

The expression "INR more than 1.4" may also be indicated as "INR>1.4".

In this embodiment, DIC is a disease or syndrome whereby large quantities of blood coagulation-accelerating substances are generated as a result of tissue damage caused by various diseases, so that the function of a coagulation system is excessively accelerated, and small thrombuses are formed in generalized blood vessel (microthrombus formation) and they clog small vessels, and at the same time, thrombocytes or coagulation factors necessary for the control of bleeding are consumed, thereby causing clotting abnormality. Specifically, as a result of fibrin formation in vascular vessel, bleeding due to consumption coagulopathy or organ failure due to microthrombus formation occurs. DIC is also referred to as disseminated intravascular coagulation syndrome or diffuse intravascular coagulation syndrome.

DIC has various types of clinical symptoms depending on the type of underlying pathogenic condition. In addition to observation of bleeding or organ symptoms, a preferred method for diagnosing an illness as DIC comprises keeping the score of DIC on the basis of several test values as described below and then diagnosing the illness as DIC when the DIC score has reached a certain level. Examples of such test values include the number of blood platelets, the concentration of fibrin/fibrinogen degradation products (hereinafter abbreviated as FDP, at times) decomposed by plasmin, a D-dimer concentration, a fibrinogen concentration, and a prothrombin time. Moreover, it is also possible to diagnose a certain condition as preDIC based on a decrease in platelets, an increase in the D-dimer or FDP concentration, and the like without keeping the DIC score (Masao Nakagawa, "Search report regarding use of criteria of disseminated intravascular coagulation (DIC)," Research Study Team of Intractable Disease (Blood Coagulation Abnormality), the Ministry of Health and Welfare, Study report 1999, 1999: 65-72; Katsumi Deguchi, "Tentative plan regarding standards for initiation of early treatment of DIC," Research Study Team of Intractable Disease (Blood Coagulation Abnormality), the Ministry of Health and Welfare, Study report 1999, 1999: 73-77; and Katsumi Nakagawa & Hajime Tsuji, "Current diagnosis of DIC—Reports on results of inquiry survey" Clinical Blood. 1999, 40: 362-364).

In this embodiment, a sepsis patient with an INR value more than 1.2, preferably more than 1.3, more preferably more than 1.4, in a plasma specimen of the patient can be called a DIC patient in a broad sense, and the medicament for therapeutic treatment and/or improvement of sepsis according to this embodiment may be used as a medicament for therapeutic treatment and/or improvement of DIC.

The medicament of this embodiment may also be used for DIC. Sepsis is also regarded as SIRS induced by critical clinical invasion from infection, and closely relates to DIC of which causative disease is an infectious disease. DIC is often developed simultaneously with sepsis, and the medicament of this embodiment may also be used for such a sepsis patient simultaneously developing DIC. In other words, the medicament of this embodiment may be used for a patient suffering from or suspected to suffer from either one of DIC and sepsis, or the both.

In this embodiment, INR can be measured, for example, as follows. Specifically, tissue thromboplastin and $Ca^{2+}$ are added to plasma (test specimen) obtained by adding sodium citrate, time (PT) required for coagulation (precipitation of fibrin) is measured, and evaluation is established on the basis of relative ratio of the time in terms of second with respect to that of a control specimen (activity ratio). The activity ratio can be obtained as "coagulation time (second) of test specimen/coagulation time (second) of control specimen", but the ratio may vary among laboratories in which the test is implemented due to difference in sensitivity of used tissue thromboplastin. The INR value was devised in order to eliminate such variation, and by evaluating PT using the INR value corrected with an international sensitivity index (henceforth also abbreviated as ISI), variation caused by difference of laboratories can be eliminated to obtain a standard result. ISI represents difference from the international standard sample. ISI is determined for every tissue thromboplastin reagent, and is attached to the reagent. Examples of the thromboplastin reagent include Thromborel S (registered trademark, Sysmex Corp.), Thromboplastin C+ (registered trademark, Sysmex Corp.), and the like, but not limited to these examples. Thromborel S (registered trademark) uses human placenta thromboplastin (ISI value is around 1.0), and thromboplastin C+ (registered trademark) uses rabbit brain thromboplastin (ISI value is about 1.8).

ISI is attached to each tissue thromboplastin reagent, and the INR value is calculated in accordance with Equation 1 mentioned above.

Although the control specimen is not particularly limited so far that the specimen is a commercially available pooled normal human plasma, there can be used commercially available pooled citrated (Na citrate) normal human plasma, and the like, available from, for example, Kojin-Bio Co., Ltd. or International Bioscience Inc.

As therapeutic treatments of sepsis, such basic treatments as mentioned below are generally performed by referring to known publications (Surviving Sepsis Campaign: International guidelines for management of severe sepsis and septic shock: Crit. Care Med., 2008, 36:296-327; Crit. Care Med., 32(3), 1250-56 (2003)), and thrombomodulin and another medicament may be used in combination. However, the other medicament used in combination is not limited to those mentioned below.

When hypotension continues in a septic shock patient even after the central venous pressure (CVP) rises to a desired value, dopamine may be administered in order to raise the average blood pressure to at least 60 mmHg. When the dopamine dose exceeds 20 μg/kg/minute, another vasopressor (usually norepinephrine) may be additionally administered.

For therapeutic treatment against causative bacteria of sepsis, an antibiotic is generally used. For the selection of the antibiotic, there is required well-grounded estimation based on suspected cause, clinical sign, knowledge concerning microorganisms and knowledge concerning pattern of sensitivity common to a specific hospital ward for inpatients, results of preliminary culture test, and the like. Intensive normalization of blood sugar level in sepsis patients improves clinical outcome of the patients in critical conditions.

When an antibiotic is used, a specimen such as blood, body fluid or wound part can be investigated, and a drug effective for the causative bacterium can be chosen. For example, in the case of septic shock of unknown cause, gentamycin or tobramycin and a third generation cephalosporin may be administered in combination. Further, when infection of resistant *Staphylococcus* or *Enterococcus* bacteria is suspected, vancomycin is additionally administered.

In general, the dose is adjusted to maintain the blood sugar level at 80 to 110 mg/dL (4.4 to 6.1 mmol/L) by continuous intravenous injection of insulin.

Since corticosteroid therapy is effective for the therapeutic treatment of sepsis, it may be administered at a supplemental dose.

To a patient of high death risk (APACHE II score≥25, multiple organ failure due to sepsis, ARDS due to septic shock or sepsis), a recombinant activated Protein C (rhAPC, drotrecogin α) may be administered when there are no contraindications (hemorrhage and the like).

Although target patients are limited, packed red blood cell transfusion may be performed aiming at Hb 7.0 to 9.0 g/dL.

In the case of impaired erythropoiesis in a sepsis patient due to renal failure, erythropoietin (EPO) may be administered.

In the case of severe sepsis, heparin may be administered at a low dose unfractionated heparin or low molecular weight heparin may be administered for prevention of DVT.

The medicament of the present invention may contain a carrier. As the carrier usable in the present invention, a water-soluble carrier is preferred, and tonicity agent, buffering agent, viscosity enhancer, surfactant, preservative, antiseptic, soothing agent, pH modifier, or the like acceptable as pharmaceutical additives is usually preferred. For example, the medicament of the present invention can be prepared by adding sucrose, glycerin, pH modifier consisting of an inorganic salt, or the like as additives. Further, if necessary, amino acids, salts, carbohydrates, surfactants, albumin, gelatin or the like may be added as disclosed in Japanese Patent Unexamined Publication Nos. 64-6219 and 6-321805. Method for adding these additives is not particularly limited. However, in the case of preparing a lyophilized product, examples include, for example, a method of mixing a solution containing at least one therapeutic agent selected from an immunosuppressant and a therapeutic agent for hematological malignancy, and a solution containing thrombomodulin, then adding additives to the mixture, and mixing the resulting mixture, and a method of mixing additives with at least one therapeutic agent selected from an immunosuppressant and a therapeutic agent for hematological malignancy dissolved in water, water for injection, or an appropriate buffer beforehand, adding a solution containing thrombomodulin to the mixture, mixing the resulting mixture to prepare a solution, and lyophilizing the solution, in manners as those commonly employed. When the medicament of the present invention is a medicament comprising a combination of the components of the medicament, each component is preferably prepared by adding a carrier according to an appropriate preparation method. The medicament of the present invention may be provided in the form of an injection, or in the form of a lyophilized preparation to be dissolved upon use.

As for preparation of the medicament of the present invention, an aqueous solution for injection can be prepared by filling a solution containing 0.1 to 10 mg of thrombomodulin, water for injection, and additives in an ampoule or vial in a volume of, for example, 0.5 to 10 mL. Examples of the preparation method also include a method of freezing such a solution, and drying the frozen solution under reduced pressure to prepare a lyophilized preparation.

The medicament of the present invention is desirably administered by parenteral administration such as intravenous administration, intramuscular administration, and subcutaneous administration. The medicament may also be administered by oral administration, intrarectal administration, intranasal administration, sublingual administration or the like. When the medicament of the present invention is a medicament comprising a combination of multiple active ingredients, each active ingredient of the medicament is preferably administered by an administration method suitable for the ingredient.

Examples of method for the intravenous administration include a method of administering a desired dose of the medicament at one time (intravenous bolus administration), and intravenous administration by drip infusion.

The method of administering a desired dose of the medicament at one time (intravenous bolus administration) is preferred from the viewpoint that the method requires only a short time for administration. Especially it is preferred in case of sepsis patients who need the urgent treatment. When the medicament is administered at one time, a period required for administration by using an injectable syringe may generally varies. In general, the period of time required for the administration is, for example, 5 minutes or shorter, preferably 3 minutes or shorter, more preferably 2 minutes or shorter, still more preferably 1 minute or shorter, particularly preferably 30 seconds or shorter, although it depends on a volume to be administered. Although the minimum administration time is not particularly limited, the period is preferably 1 second or longer, more preferably 5 seconds or longer, still more preferably 10 seconds or longer. The dose is not particularly limited so long that the dose is within the aforementioned preferred dose. Intravenous administration by drip infusion is also preferred from a viewpoint that blood level of thrombomodulin can be easily kept constant.

A daily dose of the medicament of the present invention may vary depending on age, body weight of patients, severity of disease, administration route and the like. In general, the maximum dose is preferably 20 mg/kg or less, more preferably 10 mg/kg or less, still more preferably 5 mg/kg or less, particularly preferably 2 mg/kg or less, and most preferably 1 mg/kg or less, and the minimum dose is preferably 0.001 mg/kg or more, more preferably 0.005 mg/kg or more, still more preferably 0.01 mg/kg or more, particularly preferably 0.02 mg/kg or more, and most preferably 0.05 mg/kg or more, in terms of the amount of thrombomodulin.

In the case of intravenous bolus administration, although the dose is not particularly limited so long as the dose is within the aforementioned preferred dose, the maximum daily dose is preferably 1 mg/kg or less, more preferably 0.5 mg/kg or less, still more preferably 0.1 mg/kg or less, particularly preferably 0.08 mg/kg or less, and most preferably 0.06 mg/kg or less, and the minimum dose is preferably 0.005 mg/kg or more, more preferably 0.01 mg/kg or more, still more preferably 0.02 mg/kg or more, and particularly preferably 0.04 mg/kg or more.

When the medicament of the present invention is administered to a patient having a body weight exceeding 100 kg, it may be preferably administered at a fixed dose of 6 mg, since blood volume is not proportional to the body weight, and blood volume is relatively reduced with respect to the body weight in such a patient.

In the case of continuous intravenous infusion, although the dose is not particularly limited so long as the dose is within the aforementioned preferred dose, the maximum daily dose is preferably 1 mg/kg or less, more preferably 0.5 mg/kg or less, still more preferably 0.1 mg/kg or less, particularly preferably 0.08 mg/kg or less, and most preferably 0.06 mg/kg or less, and the minimum dose is preferably 0.005 mg/kg or more, more preferably 0.01 mg/kg or more, still more preferably 0.02 mg/kg or more, and particularly preferably 0.04 mg/kg or more.

When the medicament of the present invention is administered to a patient having a body weight exceeding 100 kg, it may be preferably administered at a fixed dose of 6 mg, since blood volume is not proportional to the body weight, and blood volume is relatively reduced with respect to the body weight in such a patient.

The medicament is administered once or several times a day as required. As for administration interval, the medicament may be administered once in 2 to 14 days, preferably once in 2 to 7 days, more preferably once in 3 to 5 days.

EXPLANATION OF SEQUENCE LISTING

SEQ ID NO: 1: Amino acid sequence encoded by the gene used in production of TME456
SEQ ID NO: 2: Nucleotide sequence encoding the amino acid sequence of SEQ ID NO: 1
SEQ ID NO: 3: Amino acid sequence encoded by the gene used in production of TME456M
SEQ ID NO: 4: Nucleotide sequence encoding the amino acid sequence of SEQ ID NO: 3
SEQ ID NO: 5: Amino acid sequence encoded by the gene used in production of TMD12
SEQ ID NO: 6: Nucleotide sequence encoding the amino acid sequence of SEQ ID NO: 5
SEQ ID NO: 7: Amino acid sequence encoded by the gene used in production of TMD12M
SEQ ID NO: 8: Nucleotide sequence encoding the amino acid sequence of SEQ ID NO: 7
SEQ ID NO: 9: Amino acid sequence encoded by the gene used in production of TMD123
SEQ ID NO: 10: Nucleotide sequence encoding the amino acid sequence of SEQ ID NO: 9
SEQ ID NO: 11: Amino acid sequence encoded by the gene used in production of TMD123M
SEQ ID NO: 12: Nucleotide sequence encoding the amino acid sequence of SEQ ID NO: 11
SEQ ID NO: 13: Synthetic DNA for mutation used for carrying out site-directed mutagenesis

EXAMPLES

The present invention will be explained in detail with reference to examples and test examples. However, the present invention is not limited by these examples.

The thrombomodulin of the present invention used in the test examples was prepared according to the aforementioned method of Yamamoto et al. (the method described in Japanese Patent Unexamined Publication No. 64-6219). Preparation examples thereof are described below. Safety of the thrombomodulins obtained in these preparation examples was confirmed by single and repetitive intravenous administration tests using rats and monkeys, mouse reproduction test, local irritation test, pharmacological safety test, virus inactivation test, and the like.

Preparation Example 1

Obtaining Thrombomodulin

A highly purified product was obtained by the aforementioned method. Specifically, Chinese hamster ovary (CHO) cells were transfected with a DNA encoding the amino acid sequence of SEQ ID NO: 9 (which specifically consisted of the nucleotide sequence of SEQ ID NO: 10). From the culture of the above transformant cells, a highly purified product was obtained by collecting an active fraction with a 20 mmol/L phosphate buffer (pH 7.3) containing 50 mmol/L NaCl according to the aforementioned conventional purification method. The product was further concentrated by using an ultrafiltration membrane to obtain a thrombomodulin solution having a concentration of 11.0 mg/mL (henceforth also abbreviated as TMD123 in the specification).
<Preparation of Polysorbate Solution>
Polysorbate 80 was weighed (0.39 g) in a glass beaker, added with water for injection (30 mL), and dissolved.
<Preparation and Filling of Drug Solution>
The TMD123 solution obtained above (2239 mL, corresponding to 24.63 g of soluble thrombomodulin protein, added in a 5% excess amount) was put into a 5-L stainless steel vessel. The polysolvate solution obtained above was further added, and sodium chloride (27.9 g) was added. Water for injection (600 mL) was added, and the mixture was stirred. The mixture was adjusted to pH 6.0 by adding a 1 mol/L hydrochloric acid solution. Water for injection was further added to the mixture up to a total amount of 3940 g, and the mixture was uniformly mixed and stirred. This drug solution was subjected to filtration sterilization using a filter having a pore diameter of 0.22 μm (MCGL10S, manufactured by Millipore). The filtrate was filled in ampoules in an amount of 1.1 g each to obtain a TMD123 preparation.

Preparation Example 2

Chinese hamster ovary (CHO) cells are transfected with a DNA encoding the amino acid sequence of SEQ ID NO: 11 (which specifically consists of the nucleotide sequence of SEQ ID NO: 12), a solution of thrombomodulin purified from a culture of the above transformant cells (henceforth also abbreviated as TMD123M in the specification) by the aforementioned conventional purification method is obtained, and a TMD123M preparation is obtained in the same manner as that described above.

Preparation Example 3

Chinese hamster ovary (CHO) cells are transfected with a DNA encoding the amino acid sequence of SEQ ID NO: 1 (which specifically consists of the nucleotide sequence of SEQ ID NO: 2), thrombomodulin purified from a culture of the above transformant cells (henceforth also abbreviated as TME456 in the specification) by the aforementioned conventional purification method is obtained, and a TME456 preparation is obtained in the same manner as that described above.

Preparation Example 4

Chinese hamster ovary (CHO) cells are transfected with a DNA encoding the amino acid sequence of SEQ ID NO: 3 (which specifically consists of the nucleotide sequence of SEQ ID NO: 4), thrombomodulin purified from a culture of the above transformant cells (henceforth also abbreviated as TME456M in the specification) by the aforementioned conventional purification method is obtained, and a TME456M preparation is obtained in the same manner as that described above.

Preparation Example 5

Chinese hamster ovary (CHO) cells are transfected with a DNA encoding the amino acid sequence of SEQ ID NO: 5 (which specifically consists of the nucleotide sequence of SEQ ID NO: 6), thrombomodulin purified from a culture of the above transformant cells (henceforth also abbreviated as TMD12 in the specification) by the aforementioned conventional purification method is obtained, and a TMD12 preparation is obtained in the same manner as that described above.

Preparation Example 6

Chinese hamster ovary (CHO) cells are transfected with a DNA encoding the amino acid sequence of SEQ ID NO: 7 (which specifically consists of the nucleotide sequence of SEQ ID NO: 8), thrombomodulin purified from a culture of the above transformant cells (henceforth also abbreviated as TMD12M in the specification) by the aforementioned conventional purification method is obtained, and a TMD12M preparation is obtained in the same manner as that described above.

Preparation Example 7

Preparation of Placebo Formulation

<Preparation of Polysorbate Solution>
Polysorbate 80 was weighed (0.4 g) in a glass beaker, added with water for injection (30 mL), and dissolved.
<Preparation and Filling of Drug Solution>
Water for injection (2000 mL) was put into a 5-L stainless steel vessel. The polysolvate solution obtained above was further added. Water for injection was further added to the mixture up to a total amount of 4000 g, and the mixture was uniformly mixed and stirred. This drug solution was subjected to filtration sterilization using a filter having a pore diameter of 0.22 μm (MCGL10S, manufactured by Millipore). The filtrate was filled in ampoules in an amount of 1.1 g each to obtain a placebo preparation.

Example 1

Method for Experiment

By using TMD-123 prepared according to Preparation Example 1 as thrombomodulin, a randomized double-blind placebo-controlled study was conducted for patients with sepsis and DIC. Targeted patient number is 750 in total, and among them, 741 patients were administered with investigational drug (TMD-123 for 370 patients and placebo for 371 patients). TMD-123 was administered once a day at 0.06 mg/kg for successive 6 days via intravenous bolus administration. As the placebo, the preparation manufactured according to Preparation Example 7 was used.

For patients over the body weight of 100 kg, a fix dose of 6 mg was evenly administered once a day for successive 6 days via intravenous bolus administration in order to suppress side effects due to overdose.

A plasma INR value of a patient before the administration of the test drug was measured by the above method described as Equation 1.

Severe septic patients with organ dysfunction limited to the liver or kidney were excluded for the analysis. In patients with organ dysfunction limited to the liver or kidney, the organ dysfunction may possibly be occurred on the basis of causes not limited to sepsis such as drug-induced organ dysfunction.

Outcome after 28 days from the start of the administration was observed and a mortality rate (Mortality) of each patent group was calculated.

Further, a difference in mortality rate between TMD-123 group and placebo group was calculated as "Difference".

<Study Results>

In the group of patient without organ dysfunction, patients with the INR value of INR>1.5 in plasma before the administration of the test drug gave maximum difference (Difference: 6.1%) between the mortality rate of the group administered with TMD-123 and that of the group administered with placebo, and the group of patient with INR>1.6 gave the second highest difference in mortality rate (4.5%). In the group of patient with INR>1.4, no significantly high difference in mortality rate was absolutely or relatively observed, i.e., difference in mortality rate was about 1.7% (Table 1).

From Table 1, it is recognized that the maximum result can be found between 1.5 and 1.6 of the lower limits of INR, and when the lower limits of INR are outside the range of from 1.5 to 1.6, the difference in mortality rate was significantly decreased.

Whilst, in the group of severe septic patients having one or more organ dysfunctions selected from circulatory organ dysfunction, respiratory organ dysfunction, kidney dysfunction, and liver dysfunction, the group of patients with INR>1.4, not the group with INR>1.5, gave the maximum difference in mortality rate (9.7%), which is absolutely and relatively high difference in mortality rate as compared to the other INR lower limits (Table 2). The group of severe septic patients having one or more organ dysfunctions selected from circulatory organ dysfunction, respiratory organ dysfunction, kidney dysfunction, and liver dysfunction gave more significant difference in mortality rate between TMD-123 group and placebo group on the whole as compared to the group of patients without organ dysfunction (the former: 5.4%, the latter −1.1%).

Further, in the group of severe septic patients having one or more organ dysfunctions selected from circulatory organ dysfunction, respiratory organ dysfunction, kidney dysfunction, and liver dysfunction, the patient with $1.4<INR≤1.6$ gave absolutely remarkable difference in mortality rate as being 16.0% (Table 3). As understood from Table 3, any of the other INR upper limits gave values of the difference in mortality rate in a range of 10 to 12%, which indicates relatively recognizable remarkably high difference in mortality rate of the aforementioned group.

On the other hand, no tendency of relatively outstanding peak increase in a certain group was observed in the group of patients without organ dysfunction. The difference in mortality rate obtained was found at utmost to be 7.1% (in patient group with $1.4<INR≤1.7$) (Table 4).

TABLE 1

| INR value of plasma before administration | TMD-123 | | Placebo | | |
|---|---|---|---|---|---|
| | Number | Mortality | Number | Mortality | Difference |
| INR > 1.2 | 106 | 10/106 = 9.4% | 93 | 9/93 = 9.7% | 0.2% |
| INR > 1.3 | 81 | 6/81 = 7.4% | 75 | 6/75 = 8.0% | 0.6% |
| INR > 1.4 | 71 | 5/71 = 7.0% | 69 | 6/69 = 8.7% | 1.7% |
| INR > 1.5 | 57 | 3/57 = 5.3% | 53 | 6/53 = 11.3% | 6.1% |
| INR > 1.6 | 42 | 3/42 = 7.1% | 43 | 5/43 = 11.6% | 4.5% |
| INR > 1.7 | 29 | 3/29 = 10.3% | 27 | 1/27 = 3.7% | −6.6% |
| INR > 1.8 | 22 | 3/22 = 13.6% | 20 | 1/20 = 5.0% | −8.6% |
| INR > 1.9 | 14 | 2/14 = 14.3% | 12 | 14/32 = 8.3% | −6.0% |
| INR > 2.0 | 9 | 1/9 = 11.1% | 7 | 1/7 = 14.3% | 3.2% |

TABLE 2

| INR value of plasma before administration | TMD-123 | | Placebo | | |
|---|---|---|---|---|---|
| | Number | Mortality | Number | Mortality | Difference |
| INR > 1.2 | 184 | 44/184 = 23.9% | 186 | 55/186 = 29.6% | 5.7% |
| INR > 1.3 | 160 | 40/160 = 25.0% | 162 | 52/162 = 32.1% | 7.1% |
| INR > 1.4 | 137 | 33/137 = 24.1% | 136 | 46/136 = 33.8% | 9.7% |
| INR > 1.5 | 101 | 26/101 = 25.7% | 100 | 34/100 = 34.0% | 8.3% |
| INR > 1.6 | 81 | 23/81 = 28.4% | 77 | 26/77 = 33.8% | 5.4% |
| INR > 1.7 | 61 | 19/61 = 31.1% | 65 | 25/65 = 38.5% | 7.3% |
| INR > 1.8 | 45 | 15/45 = 33.3% | 48 | 19/48 = 39.6% | 6.3% |
| INR > 1.9 | 36 | 14/36 = 38.9% | 32 | 14/32 = 43.8% | 4.9% |
| INR > 2.0 | 27 | 13/27 = 48.1% | 25 | 14/25 = 56.0% | 7.9% |

TABLE 3

| INR value of plasma before administration | TMD-123 Number | TMD-123 Mortality | Placebo Number | Placebo Mortality | Difference |
|---|---|---|---|---|---|
| 1.6 >= INR > 1.4 | 56 | 10/56 = 17.9% | 59 | 20/59 = 33.9% | 16.0% |
| 1.7 >= INR > 1.4 | 76 | 14/76 = 18.4% | 71 | 21/71 = 29.6% | 11.2% |
| 1.8 >= INR > 1.4 | 92 | 18/92 = 19.6% | 88 | 27/88 = 30.7% | 11.1% |
| 1.9 >= INR > 1.4 | 101 | 19/101 = 18.8% | 104 | 32/104 = 30.8% | 12.0% |
| 2.0 >= INR > 1.4 | 110 | 20/110 = 18.2% | 111 | 32/111 = 28.8% | 10.6% |

TABLE 4

| INR value of plasma before administration | TMD-123 Number | TMD-123 Mortality | Placebo Number | Placebo Mortality | Difference |
|---|---|---|---|---|---|
| 1.6 >= INR > 1.4 | 29 | 2/29 = 6.9% | 26 | 1/26 = 3.8% | −3.1% |
| 1.7 >= INR > 1.4 | 42 | 2/42 = 4.8% | 42 | 5/42 = 11.9% | 7.1% |
| 1.8 >= INR > 1.4 | 49 | 2/49 = 4.1% | 49 | 5/49 = 10.2% | 6.1% |
| 1.9 >= INR > 1.4 | 57 | 3/57 = 5.3% | 57 | 5/57 = 8.8% | 3.5% |
| 2.0 >= INR > 1.4 | 62 | 4/62 = 6.5% | 62 | 5/62 = 8.1% | 1.6% |

INDUSTRIAL APPLICABILITY

The medicament of the present invention containing thrombomodulin is useful as a medicament enabling effective therapeutic treatment and/or improvement of sepsis in a severe septic patient, wherein a INR value of a plasma specimen obtained from said patient is more than 1.4.

What is claimed is:

1. A method for therapeutic treatment of sepsis, which comprises the step of: intravenously administering thrombomodulin to a patient with severe sepsis accompanied with one or more organ dysfunctions selected from the group consisting of respiratory organ dysfunction and circulatory organ dysfunction, wherein a value of International Normalized Ratio (INR) of a plasma specimen obtained from said patient is more than 1.4, wherein said thrombomodulin is administered at a dose of 0.04-0.08 mg/kg/day for 6 days.

* * * * *

SEQUENCE LISTING

```
<160> NUMBER OF SEQ ID NOS: 13

<210> SEQ ID NO 1
<211> LENGTH: 132
<212> TYPE: PRT
<213> ORGANISM: human

<400> SEQUENCE: 1

Met Leu Gly Val Leu Val Leu Gly Ala Leu Ala Leu Ala Gly Leu Gly
1               5                   10                  15

Phe Pro Asp Pro Cys Phe Arg Ala Asn Cys Glu Tyr Gln Cys Gln Pro
                20                  25                  30

Leu Asn Gln Thr Ser Tyr Leu Cys Val Cys Ala Glu Gly Phe Ala Pro
            35                  40                  45

Ile Pro His Glu Pro His Arg Cys Gln Met Phe Cys Asn Gln Thr Ala
        50                  55                  60

Cys Pro Ala Asp Cys Asp Pro Asn Thr Gln Ala Ser Cys Glu Cys Pro
65                  70                  75                  80

Glu Gly Tyr Ile Leu Asp Asp Gly Phe Ile Cys Thr Asp Ile Asp Glu
                85                  90                  95

Cys Glu Asn Gly Gly Phe Cys Ser Gly Val Cys His Asn Leu Pro Gly
            100                 105                 110

Thr Phe Glu Cys Ile Cys Gly Pro Asp Ser Ala Leu Val Arg His Ile
        115                 120                 125

Gly Thr Asp Cys
    130
```

<210> SEQ ID NO 2
<211> LENGTH: 396
<212> TYPE: DNA
<213> ORGANISM: human

<400> SEQUENCE: 2

```
atgcttgggg tcctggtcct tggcgcgctg ccctggccg gctggggtt ccccgacccg        60 tgcttcagag ccaactgcga gtaccagtgc cagcccctga ccaaactag ctacctctgc      120 gtctgcgccg agggcttcgc gcccattccc cacgagccgc acaggtgcca gatgttttgc    180
aaccagactg cctgtccagc cgactgcgac cccaacaccc aggctagctg tgagtgccct    240
gaaggctaca tcctggacga cggtttcatc tgcacggaca tcgacgagtg cgaaaacggc    300
ggcttctgct ccggggtgtg ccacaacctc cccggtacct tcgagtgcat ctgcgggccc    360
gactcggccc ttgtccgcca cattggcacc gactgt                              396
```

<210> SEQ ID NO 3
<211> LENGTH: 132
<212> TYPE: PRT
<213> ORGANISM: human

<400> SEQUENCE: 3

```
Met Leu Gly Val Leu Val Leu Gly Ala Leu Ala Leu Ala Gly Leu Gly
1               5                   10                  15

Phe Pro Asp Pro Cys Phe Arg Ala Asn Cys Glu Tyr Gln Cys Gln Pro
            20                  25                  30

Leu Asn Gln Thr Ser Tyr Leu Cys Val Cys Ala Glu Gly Phe Ala Pro
        35                  40                  45

Ile Pro His Glu Pro His Arg Cys Gln Met Phe Cys Asn Gln Thr Ala
    50                  55                  60

Cys Pro Ala Asp Cys Asp Pro Asn Thr Gln Ala Ser Cys Glu Cys Pro
65                  70                  75                  80

Glu Gly Tyr Ile Leu Asp Asp Gly Phe Ile Cys Thr Asp Ile Asp Glu
                85                  90                  95

Cys Glu Asn Gly Gly Phe Cys Ser Gly Val Cys His Asn Leu Pro Gly
            100                 105                 110

Thr Phe Glu Cys Ile Cys Gly Pro Asp Ser Ala Leu Ala Arg His Ile
        115                 120                 125

Gly Thr Asp Cys
    130
```

<210> SEQ ID NO 4
<211> LENGTH: 396
<212> TYPE: DNA
<213> ORGANISM: human

<400> SEQUENCE: 4

```
atgcttgggg tcctggtcct tggcgcgctg ccctggccg gctggggtt ccccgacccg        60 tgcttcagag ccaactgcga gtaccagtgc cagcccctga ccaaactag ctacctctgc      120 gtctgcgccg agggcttcgc gcccattccc cacgagccgc acaggtgcca gatgttttgc    180
aaccagactg cctgtccagc cgactgcgac cccaacaccc aggctagctg tgagtgccct    240
gaaggctaca tcctggacga cggtttcatc tgcacggaca tcgacgagtg cgaaaacggc    300
ggcttctgct ccggggtgtg ccacaacctc cccggtacct tcgagtgcat ctgcgggccc    360
gactcggccc ttgcccgcca cattggcacc gactgt                              396
```

<210> SEQ ID NO 5
<211> LENGTH: 480
<212> TYPE: PRT
<213> ORGANISM: human

<400> SEQUENCE: 5

```
Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
    210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
    290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
        355                 360                 365

Cys Phe Arg Ala Asn Cys Glu Tyr Gln Cys Gln Pro Leu Asn Gln Thr
    370                 375                 380
```

```
Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
            405                 410                 415

Cys Asp Pro Asn Thr Gln Ala Ser Cys Glu Cys Pro Glu Gly Tyr Ile
        420                 425                 430

Leu Asp Asp Gly Phe Ile Cys Thr Asp Ile Asp Glu Cys Glu Asn Gly
    435                 440                 445

Gly Phe Cys Ser Gly Val Cys His Asn Leu Pro Gly Thr Phe Glu Cys
450                 455                 460

Ile Cys Gly Pro Asp Ser Ala Leu Val Arg His Ile Gly Thr Asp Cys
465                 470                 475                 480

<210> SEQ ID NO 6
<211> LENGTH: 1440
<212> TYPE: DNA
<213> ORGANISM: human

<400> SEQUENCE: 6
atgcttgggg tcctggtcct tggcgcgctg gccctggccg gcctgggggtt ccccgcaccc      60 gcagagccgc agccgggtgg cagccagtgc gtcgagcacg actgcttcgc gctctacccg     120
ggccccgcga ccttcctcaa tgccagtcag atctgcgacg actgcggggg ccacctaatg     180
acagtgcgct cctcggtggc tgccgatgtc atttccttgc tactgaacgg cgacggcggc     240
gttggccgcc ggcgcctctg gatcggcctg cagctgccac ccggctgcgg cgaccccaag     300
cgcctcgggc ccctgcgcgg cttccagtgg gttacgggag acaacaacac cagctatagc     360
aggtgggcac ggctcgacct caatggggct cccctctgcg gccgttgtg cgtcgctgtc      420 tccgctgctg aggccactgt gcccagcgag ccgatctggg aggagcagca gtgcgaagtg     480
aaggccgatg gcttcctctg cgagttccac ttcccagcca cctgcaggcc actggctgtg     540
gagcccggcg ccgcggctgc cgccgtctcg atcacctacg gcaccccgtt cgcggcccgc     600
ggagcggact ccaggcgct gccggtgggc agctccgccg cggtggctcc cctcggctta    660
cagctaatgt gcaccgcgcc gcccggagcg gtccaggggc actgggccag ggaggcgccg     720
ggcgcttggg actgcagcgt ggagaacggc ggctgcgagc acgcgtgcaa tgcgatccct     780
ggggctcccc gctgccagtg cccagccggc gccgccctgc aggcagacgg cgctcctgc     840 accgcatccg cgacgcagtc ctgcaacgac ctctgcgagc acttctgcgt tcccaacccc    900
gaccagccgg gctcctactc cgtgcatgtgc gagaccggct accggctggc ggccgaccaa    960
caccggtgcg aggacgtgga tgactgcata ctggagccca gtccgtgtcc gcagcgctgt  1020
gtcaacacac agggtggctt cgagtgccac tgctacccta actacgacct ggtggacggc    1080
gagtgtgtgg agcccgtgga cccgtgcttc agagccaact gcgagtacca gtgccagccc   1140
ctgaaccaaa ctagctacct ctgcgtctgc gccgagggct cgcgcccat tcccacgag    1200 ccgcacaggt gccagatgtt ttgcaaccag actgcctgtc cagccgactg cgaccccaac  1260
acccaggcta ctgtgagtg ccctgaaggc tacatcctgg acgacggttt catctgcacg   1320
gacatcgacg agtgcgaaaa cggcggcttc tgctccgggg tgtgccacaa cctccccggt   1380
accttcgagt gcatctgcgg gcccgactcg gcccttgtcc gccacattgg caccgactgt  1440

<210> SEQ ID NO 7
<211> LENGTH: 480
<212> TYPE: PRT
```

-continued

<213> ORGANISM: human

<400> SEQUENCE: 7

```
Met Leu Gly Val Leu Val Leu Gly Ala Leu Ala Leu Ala Gly Leu Gly
 1               5                  10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
    210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
    290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
        355                 360                 365

Cys Phe Arg Ala Asn Cys Glu Tyr Gln Cys Gln Pro Leu Asn Gln Thr
    370                 375                 380

Ser Tyr Leu Cys Val Cys Ala Glu Gly Phe Ala Pro Ile Pro His Glu
385                 390                 395                 400
```

| | | | | | | | | | | | |
|---|---|---|---|---|---|---|---|---|---|---|---|
|Pro|His|Arg|Cys|Gln|Met|Phe|Cys|Asn|Gln|Thr|Ala|Cys|Pro|Ala|Asp|
| | | | |405| | | |410| | | |415| | | |

Cys Asp Pro Asn Thr Gln Ala Ser Cys Glu Cys Pro Glu Gly Tyr Ile
            420                      425                      430

Leu Asp Asp Gly Phe Ile Cys Thr Asp Ile Asp Glu Cys Glu Asn Gly
          435                      440                      445

Gly Phe Cys Ser Gly Val Cys His Asn Leu Pro Gly Thr Phe Glu Cys
    450                      455                      460

Ile Cys Gly Pro Asp Ser Ala Leu Ala Arg His Ile Gly Thr Asp Cys
465                    470                    475                  480

<210> SEQ ID NO 8
<211> LENGTH: 1440
<212> TYPE: DNA
<213> ORGANISM: human

<400> SEQUENCE: 8

```
atgcttgggg tcctggtcct tggcgcgctg gccctggccg gctgggggtt ccccgcaccc      60
gcagagccgc agccgggtgg cagccagtgc gtcgagcacg actgcttcgc gctctacccg     120
ggccccgcga ccttcctcaa tgccagtcag atctgcgacg actgcggggc cacctaatg      180
acagtgcgct cctcggtggc tgccgatgtc atttccttgc tactgaacgg cgacggcggc     240
gttggccgcc ggcgcctctg gatcggcctg cagctgccac ccggctgcgg cgaccccaag     300
cgcctcgggc ccctgcgcgg cttccagtgg gttacgggag acaacaacac cagctatagc     360
aggtgggcac ggctcgacct caatggggct cccctctgcg cccgttgtg cgtcgctgtc      420
tccgctgctg aggccactgt gcccagcgag ccgatctggg aggagcagca gtgcgaagtg     480
aaggccgatg cttcctctg cgagttccac ttcccagcca cctgcaggcc actggctgtg     540
gagcccggcg ccgcggctgc cgccgtctcg atcacctacg caccccgtt cgcggcccgc     600
ggagcggact tccaggcgct gccggtgggc agctccgccg cggtggctcc cctcggctta     660
cagctaatgt gcaccgcgcc gccggagcg gtccaggggc actgggccag ggaggcgccg     720
ggcgcttggg actgcagcgt ggagaacggc ggctgcgagc acgcgtgcaa tgcgatccct     780
ggggctcccc gctgccagtg cccagccggc cgccctgc aggcagacgg cgctcctgc       840
accgcatccg cgacgcagtc ctgcaacgac ctctgcgagc acttctgcgt tcccaacccc     900
gaccagccgg gctcctactc gtgcatgtgc gagaccggct accggctggc ggccgaccaa     960
caccggtgcg aggacgtgga tgactgcata ctggagccca gtccgtgtcc gcagcgctgt    1020
gtcaacacac agggtggctt cgagtgccac tgctaccct actacgacct ggtggacggc    1080
gagtgtgtgg agcccgtgga cccgtgcttc agagccaact gcgagtacca gtgccagccc    1140
ctgaaccaaa ctagctacct ctgcgtctgc gccgagggct cgcgcccat tcccacgag     1200
ccgcacaggt gccagatgtt ttgcaaccag actgcctgtc agccgactg cgaccccaac    1260
acccaggcta gctgtgagtg ccctgaaggc tacatcctgg acgacggtttt catctgcacg    1320
gacatcgacg agtgcgaaaa cggcggcttc tgctccgggg tgtgccacaa cctccccggt    1380
accttcgagt gcatctgcgg gcccgactcg gccttgccc gccacattgg caccgactgt    1440
```

<210> SEQ ID NO 9
<211> LENGTH: 516
<212> TYPE: PRT
<213> ORGANISM: human

<400> SEQUENCE: 9

-continued

```
Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
            35                  40                  45

Ser Gln Ile Cys Asp Gly Leu Arg Gly His Leu Met Thr Val Arg Ser
50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
            195                 200                 205

Val Gly Ser Ser Ala Ala Val Ala Pro Leu Gly Leu Gln Leu Met Cys
210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
275                 280                 285

Asn Asp Leu Cys Glu His Phe Cys Val Pro Asn Pro Asp Gln Pro Gly
            290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
            355                 360                 365

Cys Phe Arg Ala Asn Cys Glu Tyr Gln Cys Gln Pro Leu Asn Gln Thr
            370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
```

```
                420              425              430
Leu Asp Asp Gly Phe Ile Cys Thr Asp Ile Asp Glu Cys Glu Asn Gly
            435                  440                  445

Gly Phe Cys Ser Gly Val Cys His Asn Leu Pro Gly Thr Phe Glu Cys
        450                  455                  460

Ile Cys Gly Pro Asp Ser Ala Leu Val Arg His Ile Gly Thr Asp Cys
465                  470                  475                  480

Asp Ser Gly Lys Val Asp Gly Gly Asp Ser Gly Ser Gly Glu Pro Pro
                485                  490                  495

Pro Ser Pro Thr Pro Gly Ser Thr Leu Thr Pro Pro Ala Val Gly Leu
                500                  505                  510

Val His Ser Gly
        515

<210> SEQ ID NO 10
<211> LENGTH: 1548
<212> TYPE: DNA
<213> ORGANISM: human

<400> SEQUENCE: 10
atgcttgggg tcctggtcct tggcgcgctg gccctggccg gctggggtt  ccccgcaccc    60 gcagagccgc agccgggtgg cagccagtgc gtcgagcacg actgcttcgc gctctacccg   120
ggccccgcga ccttcctcaa tgccagtcag atctgcgacg gactgcgggg ccacctaatg   180
acagtgcgct cctcggtggc tgccgatgtc atttccttgc tactgaacgg cgacggcggc   240
gttggccgcc ggcgcctctg gatcggcctg cagctgccac ccggctgcgg cgaccccaag   300
cgcctcgggc cctgcgcgg  cttccagtgg gttacgggag acaacaacac cagctatagc   360
aggtgggcac ggctcgacct caatggggct cccctctgcg cccgttgtg  cgtcgctgtc   420 tccgctgctg aggccactgt gcccagcgag ccgatctggg aggagcagca gtgcgaagtg   480
aaggccgatg gcttcctctg cgagttccac ttcccagcca cctgcaggcc actggctgtg   540
gagcccggcg ccgcggctgc cgccgtctcg atcacctacg caccccgtt  cgcggcccgc   600 ggagcggact tccaggcgct gccggtgggc agctccgccg cggtggctcc cctcggctta   660
cagctaatgt gcaccgcgcc gccggagcg  gtccaggggc actgggccag ggaggcgccg   720
ggcgcttggg actgcagcgt ggagaacggc ggctgcgagc acgcgtgcaa tgcgatccct   780
ggggctcccc gctgccagtg cccagccggc gccgccctgc aggcagacgg cgcctcctgc   840
accgcatccg cgacgcagtc ctgcaacgac ctctgcgagc acttctgcgt tcccaacccc   900
gaccagccgg gctcctactc gtgcatgtgc gagaccggct accggctggc ggccgaccaa   960
caccggtgcg aggacgtgga tgactgcata ctggagccca gtccgtgtcc gcagcgctgt  1020
gtcaacacac agggtggctt cgagtgccac tgctacccta actacgacct ggtggacggc  1080
gagtgtgtgg agcccgtgga cccgtgcttc agagccaact gcgagtacca gtgccagccc  1140
ctgaaccaaa ctagctacct ctgcgtctgc gccgagggct cgcgcccat  tccccacgag  1200 ccgcacaggt gccagatgtt ttgcaaccag actgcctgtc agccgactg  cgaccccaac  1260 acccaggcta gctgtgagtg ccctgaaggc tacatcctgg acgacggttt catctgcacg  1320
gacatcgacg agtgcgaaaa cggcggcttc tgctccgggg tgtgccacaa cctccccggt  1380
accttcgagt gcatctgcgg gccgactcg  gccttgtcc  gccacattgg caccgactgt  1440
gactccggca aggtgacgg  tggcgacagc ggctctggcg agcccccgcc cagcccgacg  1500
cccggctcca ccttgactcc tccggccgtg gggctcgtgc attcgggc             1548
```

<210> SEQ ID NO 11
<211> LENGTH: 516
<212> TYPE: PRT
<213> ORGANISM: human

<400> SEQUENCE: 11

```
Met Leu Gly Val Leu Val Leu Gly Ala Leu Ala Leu Ala Gly Leu Gly
1               5                   10                  15

Phe Pro Ala Pro Ala Glu Pro Gln Gly Gly Ser Gln Cys Val Glu
            20                  25                  30

His Asp Cys Phe Ala Leu Tyr Pro Gly Pro Ala Thr Phe Leu Asn Ala
            35                  40                  45

Ser Gln Ile Cys Asp Gly Leu Arg Gly His Leu Met Thr Val Arg Ser
        50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
        130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
            195                 200                 205

Val Gly Ser Ser Ala Ala Val Ala Pro Leu Gly Leu Gln Leu Met Cys
        210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
        290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
            355                 360                 365

Cys Phe Arg Ala Asn Cys Glu Tyr Gln Cys Gln Pro Leu Asn Gln Thr
```

```
            370                 375                 380
Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
                420                 425                 430

Leu Asp Asp Gly Phe Ile Cys Thr Asp Ile Asp Glu Cys Glu Asn Gly
            435                 440                 445

Gly Phe Cys Ser Gly Val Cys His Asn Leu Pro Gly Thr Phe Glu Cys
        450                 455                 460

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
                485                 490                 495

Pro Ser Pro Thr Pro Gly Ser Thr Leu Thr Pro Pro Ala Val Gly Leu
                500                 505                 510

Val His Ser Gly
        515

<210> SEQ ID NO 12
<211> LENGTH: 1548
<212> TYPE: DNA
<213> ORGANISM: human

<400> SEQUENCE: 12
atgcttgggg tcctggtcct tggcgcgctg ccctggccg gcctggggtt ccccgcaccc      60
gcagagccgc agccgggtgg cagccagtgc gtcgagcacg actgcttcgc gctctacccg     120
ggccccgcga ccttcctcaa tgccagtcag atctgcgacg gactgcgggg ccacctaatg     180
acagtgcgct cctcggtggc tgccgatgtc atttccttgc tactgaacgg cgacggcggc     240
gttggccgcc ggcgcctctg gatcggcctg cagctgccac ccggctgcgg cgaccccaag     300
cgcctcgggc cctgcgcgg cttccagtgg gttacgggag acaacaacac cagctatagc      360
aggtgggcac ggctcgacct caatgggct ccccctctgcg cccgttgtg cgtcgctgtc       420 tccgctgctg aggccactgt gcccagcgag ccgatctggg aggagcagca gtgcgaagtg     480
aaggccgatg gcttcctctg cgagttccac ttcccagcca cctgcaggcc actggctgtg     540
gagcccggcg ccgcggctgc cgccgtctcg atcacctacg gcaccccgtt cgcggcccgc     600
ggagcggact ccaggcgct gccggtgggc agctccgccg cggtggctcc cctcggctta      660
cagctaatgt gcaccgcgcc gcccggagcg gtccaggggc actgggccag ggaggcgccg     720
ggcgcttggg actgcagcgt ggagaacggc ggctgcgagc acgcgtgcaa tgcgatccct     780
ggggctcccc gctgccagtg cccagccggc gccgccctgc aggcagacgg cgctcctgc      840 accgcatccg cgacgcagtc ctgcaacgac ctctgcgagc acttctgcgt tcccaacccc     900
gaccagccgg gctcctactc gtgcatgtgc gagaccggct accggctggc ggccgaccaa     960
caccggtgcg aggacgtgga tgactgcata ctggagccca gtccgtgtcc gcagcgctgt    1020
gtcaacacac agggtggctt cgagtgccac tgctacccta ctacgacct ggtggacggc     1080 gagtgtgtgg agcccgtgga cccgtgcttc agagccaact gcgagtacca gtgccagccc    1140
ctgaaccaaa ctagctacct ctgcgtctgc gccgagggct cgcgcccat tccccacgag    1200 ccgcacaggt gccagatgtt ttgcaaccag actgcctgtc cagccgactg cgaccccaac    1260
```

-continued

```
acccaggcta gctgtgagtg ccctgaaggc tacatcctgg acgacggttt catctgcacg    1320
gacatcgacg agtgcgaaaa cggcggcttc tgctccgggg tgtgccacaa cctccccggt    1380
accttcgagt gcatctgcgg gcccgactcg gcccttgccc gccacattgg caccgactgt    1440
gactccggca aggtggacgg tggcgacagc ggctctggcg agcccccgcc cagcccgacg    1500
cccggctcca ccttgactcc tccggccgtg gggctcgtgc attcgggc                 1548
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
    DNA

<400> SEQUENCE: 13
aatgtggcgg gcaagggccg a                                              21